United States Patent
Meece et al.

(10) Patent No.: US 9,347,965 B1
(45) Date of Patent: May 24, 2016

(54) AUTOSAMPLER WITH ENHANCED EXPANSION CAPABILITY

(71) Applicant: Professional Technical Services, Fairfield, OH (US)

(72) Inventors: Douglas A. Meece, Norwood, OH (US); Richard C. Kirkland, White Lake, MI (US)

(73) Assignee: EST Analytical, Inc., Fairfield, OH (US)

( * ) Notice: Subject to any disclaimer, the term of this patent is extended or adjusted under 35 U.S.C. 154(b) by 156 days.

(21) Appl. No.: 14/208,229

(22) Filed: Mar. 13, 2014

(51) Int. Cl.
*G01N 35/10* (2006.01)

(52) U.S. Cl.
CPC ...................................... *G01N 35/10* (2013.01)

(58) Field of Classification Search
None
See application file for complete search history.

(56) References Cited

U.S. PATENT DOCUMENTS

| | | | |
|---|---|---|---|
| 5,441,700 | A | 8/1995 | Markelov |
| 7,803,635 | B1 | 9/2010 | Meece |
| 8,075,842 | B1 | 12/2011 | Meece |
| 8,092,744 | B1 | 1/2012 | Meece |
| 2006/0088940 | A1* | 4/2006 | Feingold ................. G01N 1/31 436/47 |

OTHER PUBLICATIONS

EST Centurion purge and trap autosampler op-manual; EST Analytical, Inc. (Oct. 2011).
EST Cobra autosampler op-manual; EST Analytical, Inc. (before 2012).
EST Centurion purge and trap autosampler wiring diagram; EST Analytical, Inc. (Oct. 2011).

* cited by examiner

*Primary Examiner* — Robert R Raevis
(74) *Attorney, Agent, or Firm* — Frederick H. Gribbell

(57) ABSTRACT

A chemical autosampler is disclosed having a main control unit with a processing circuit that communicates with various electronic modules using wireless communications signals, which allows for easy expansion of the capabilities of the basic autosampler unit. The main control unit resides on a longitudinal rail module that allows many various accessory modules to be physically mounted to the rail. There is a head module that includes the sampling syringe, and also includes transport motors that allow the head module to move in three axes. The head module includes its own processing circuit to control various solenoids and valves to properly move liquids and gasses for the sampling procedures, and to control the various transport motors. The autosampler also includes a control routine to automatically detect and calibrate the position of each of the accessory modules that are installed by a user on the rail module.

18 Claims, 15 Drawing Sheets

AUTOSAMPLER WITH ENHANCED EXPANSION CAPABILITY

TECHNICAL FIELD

The technology disclosed herein relates generally to chemical sampling equipment and is particularly directed to automatic analytical samplers of the type which sample headspace gasses, liquids, and solids, usually contained in vials. Embodiments are specifically disclosed as a chemical autosampler having a main control unit with a processing circuit that communicates with various electronic modules using wireless communications signals which allows for easy expansion of the capabilities of the basic autosampler unit. The main control unit resides on a longitudinal rail module that allows many various accessory modules to be physically mounted to the rail.

In the new design autosampler of the technology disclosed herein, there is a head module that includes the sampling syringe, and also includes transport motors that allow the head module to move in three axes. The head module communicates wirelessly to the main control unit, and also to any of the various electronic modules, as needed. The head module includes its own processing circuit to control the various solenoids and valves to properly move liquids and gasses for the sampling procedures, and to control the various transport motors.

The autosampler also includes a control routine to automatically detect and calibrate the position of each of the accessory modules that are installed by a user onto the rail module. Some of the accessory modules are "smart" devices that include processing circuits and wireless communication circuits. Some of the accessory modules are "dumb" devices, such as sample trays that hold several sample vials; however, such dumb devices need to have their physical positions on the rail determined with some precision, and the calibration control routine uses identification markers and an optical sensor to make those determinations, in conjunction with the head module.

STATEMENT REGARDING FEDERALLY SPONSORED RESEARCH OR DEVELOPMENT

None.

BACKGROUND

Analytic chemical sampling equipment has been available for years, including equipment that performs automatic sampling of multiple vials that each contain chemical samplers. Such equipment of often referred to as an "autosampler," and typically includes a movable head that has a syringe that can be lowered into one of the sample vials to extract some of the chemical sample contained within that vial. EST Analytical, Inc. has sold autosamplers under various trademark names, including the CENTURION and the COBRA autosampler.

EST Analytical, Inc. also has patented various types of chemical handling equipment, including samplers. A list of such patents is provided, below.

Referring now to FIG. 1, the main electrical and electronic components of an EST "Centurion" are depicted, generally designated by the reference numeral 10. This Centurion device has a main processor board designated by the reference numeral 20, an operating system board at reference numeral 30, a digital input/output board (I/O board) at reference numeral 50, a "PWM" board (produces pulse-width modulated current) at reference numeral 60, a first motion control board at 70 and a second motion control board at 80.

The main processor board 20 includes a microprocessor circuit 22, a memory circuit 24, an input/output interface circuit 26, and a number of conductive pathways at 28 that transfer input and output signals to external devices. The processing circuit 22 can be virtually any type of computer device, and typically would be a microprocessor or a microcontroller. The memory circuit 24 will contain random access memory (RAM) and typically would also include read only memory (ROM), usually including some that is programmable, such as EEPROM devices. The I/O interface 26 will be able to interface both analog and digital signals.

The operating system board 30 essentially is a personal computer on a single circuit board. It includes a microprocessor 32, system memory 34, and I/O interface circuitry at 36. Part of the I/O interface circuitry is for outputting a signal to a display monitor, which is depicted as a user monitor 40. This would be a display screen in which the user can diagrammatically see the system components. The I/O interface 36 also has signals going to a LAN (local area network) output circuit 38, which can be connected to the Internet at 42. In the EST Centurion unit, the LAN circuit is an Ethernet circuit. A multi-conductor flat cable 90 is used to connect the signals between the operating system board 30 and the main processor board 20.

The digital I/O board 50 also contains a processing circuit 52 and memory circuit 54, along with an input/output interface circuit 56. The digital I/O board 50 controls many valves and solenoids, grouped on FIG. 1 in the block designated by the reference numeral 58. These valves and solenoids are the devices that control the fluidic flow pathways throughout the autosampler device that makes up the heart of the EST Centurion 10. Another multi-conductor flat cable 92 is used to connect the signals between the digital I/O board 50 and the main processor board 20. The digital I/O board 50 also has an output to a "GC" device 44. A GC device is an acronym for a Gas Chromatograph, which is a standard analytical instrument used for chemical analyses.

The PWM board 60 includes a processing circuit 62, a memory circuit 64, and a I/O interface circuit 66. This board controls a number of heaters grouped on FIG. 1 in the block 68, and also has other analog signals, including analog input from a temperature sensor 69. The heaters are typically energized using pulse-width modulation control signals, which are essentially square waves having a varying duty cycle, as controlled by the PWM board 60. There is a multi-conductor flat cable 94 that carries the signals between the PWM board 60 and the main processor 20.

The two motion control boards 70 and 80 are essentially identical in form, each having a micro-processor circuit and memory circuit as well as an input/output interface circuit. On the first motion control board 70, the processing circuit is at 72, the memory circuit is 74, and the I/O interface is 76. These devices control three different stepper motors, grouped on FIG. 1 by the reference numeral 78. These separate motors control the three axes of movement of the head module that contains the syringe that does the actual sampling of the chemicals that are placed in vials. A multi-conductor flat cable 96 carries the signals between the first motion control board 70 and the main processor board 20. However, it should be noted that this flat cable must be shielded, because otherwise the electromagnetic interference (EMI) created by the power signals energizing the heater 68 and the various motors 78 and 88 in the Centurion system will induce noise into the control signal wires that are inside the flat cable 96. Without the shield, the Centurion system would never work properly in all probability, because the interference produced by the power signals would mask the actual low-voltage control signals that run between the microprocessors on the motion control boards and the main processor board.

The second motion control board 80 has a processing circuit 82, a memory circuit 84, and an I/O interface circuit 86. This device controls three other motors in the system, grouped on FIG. 1 under the reference numeral 88. In a standard Centurion unit sold by EST Analytics, there is a gripper motor, a syringe motor, and a "soil elevator" motor, used for sampling solid materials. There is a multi-conductor flat cable 98 that runs between the first and second boards 70 and 80. It should be noted that flat cable 98 could instead have been run directly back to the main processor board 20, but that would have been a longer run, and this cable is also subject to interference from the power alternating current ("pulsed") signals that run throughout the Centurion unit. Therefore, flat cable 98 is also shielded, even though it has a shorter physical run. These shielded cables are an extra expense that is often found in industrial equipment and laboratory equipment, because power signals are also found in those same environments.

Referring now to FIG. 2, an entire EST Centurion unit 10 is depicted, and shows some of the main electrical components. Easily seen in this view are a power supply 5, the digital I/O board 50, the operating system board 30, and one of the motion control boards 80. The motors 78 and 88 are placed inside the head module, approximately located as indicated on the figure. The valves and solenoids 58 and heaters 68, as well as the temperature sensor 69, are all located inside a separate compartment along with the plumbing that runs between such valves, solenoids, and other devices in the Centurion unit, as indicated by the arrow on FIG. 2. The user monitor 40 is also illustrated, and sits above the overall enclosure.

Referring now to FIG. 3, a more close-view of the Centurion unit's electrical control compartment is illustrated. The main processor board 20 is mounted beneath the operating system board 30, and the first motion control board 70 is mounted beneath the second motion control board 80. The digital I/O board 50 is mounted by itself, and the PWM board 60 is mounted off to the side, as shown. The shielded flat cables 96 and 98, are illustrated in this view. It should be noted that there are other flat cables in this EST Centurion unit, but they are not illustrated for purposes of clarity. In addition, there are dozens of other single conductor cables that run throughout the unit, mainly carrying power signals, or other types of control signals that are not grouped together in flat cables. These additional cables are also not illustrated, for purposes of clarity.

The two shielded flat cables 96 and 98 that are illustrated on FIG. 3 carry control signals, but they also run to the two motion control boards 70 and 80 which output power signals to the stepper motors 78, 88. Each stepper motor can draw up to two amperes maximum, and as noted above, the stepper motor signals are essentially a series of square waves, so they generate quite a large amount of EMI as they make the transitions from zero volts to full voltage. In addition, the heating elements in the heater 68 can draw up to three amperes per heating element, and those signals are also pulse-width modulated signals that generate a large amount of EMI. Simple stated, the autosampler device is a very noisy device when it comes to electromagnetic interference. When designing such equipment, particular attention must be devoted to protecting the control signals from that EMI noise, and in the case of the flat cables 96 and 98, shielding was needed. In essence, those two flat cables are the weakest link with regard to EMI noise tolerance.

The EST Centurion device 10 is designed for some expansion capability, in which a third motion control board can be mounted above the second motion control board 80. In that way additional stepper motors can be controlled, if a particular customer wants additional capabilities beyond the six stepper motors that are listed on FIG. 1. As would be expected, another shielded flat cable would be needed to run to that third motion control board, since that third board will induce yet more electrical noise into the Centurion environment. In that situation, the control signals for the third motion control board would run from the processor board 20, through the flat cable 96, through the first motion control board 70, through the second shielded flat cable 98, through the second motion control board 80, and then through a third shielded flat cable (not shown on FIG. 3), and finally to the third motion control board (also not shown on FIG. 3). While the capability for expansion exists in the Centurion unit, it becomes a rather complicated affair from a physical hardware and mounting of components standpoint.

It should be noted here that EST Analytics also sells a smaller version of an autosampler under the trademark name "COBRA." The Cobra system has a motherboard and uses a multi-conductor flat cable to run signals to a motion control board. This device is a relatively low-power device, and has motors that only draw one ampere maximum per stepper motor. The motor pulse signals are also run in the same multi-conductor flat cable as the other control signals, so the system is fairly well maxed out with respect to any type of future expansion capability. Any higher amperage in the motor drive signals and there would be too much crosstalk between the flat cable conductors, and the control signals would be swamped by EMI. Another limitation at this time in the Cobra system is that only one of the three axes stepper motors is run at a time, mainly to eliminate additional crosstalk between the conductors. In addition, the system is not expandable, and it does not power any heaters. The Cobra system is rather limited as compared to the Centurion system.

The Centurion system can run multiple axes motors simultaneously, and as noted above, it can be expanded to have a third motion control circuit board. It also is a higher power device, drawing up to two amperes per stepper motor, and it can have heaters.

SUMMARY

Accordingly, it is an advantage to provide a chemical autosampler having a main control unit that communicates with various electronic modules using wireless communications signals that allow for easy expansion of the capabilities of the basic autosampler unit.

It is another advantage to provide a chemical autosampler that includes a longitudinal rail that allows various accessory modules to be mounted to that rail, specifically by choice of the user of such a system.

It is yet another advantage to provide a chemical autosampler that includes an automatic position calibration routine to determine substantially the precise locations of accessory modules that have been mounted by a user to the longitudinal rail that makes up the main portion of the autosampler.

Additional advantages and other novel features will be set forth in part in the description that follows and in part will become apparent to those skilled in the art upon examination of the following or may be learned with the practice of the technology disclosed herein.

To achieve the foregoing and other advantages, and in accordance with one aspect, an automated chemical sampling apparatus is provided, which comprises: (a) a main computer station, having a first processing circuit, a first memory circuit, and a first communications circuit; (b) a longitudinal member extending in a substantially horizontal direction and that is shaped and sized to receive at least one mounting leg of an accessory module; (c) a head module that includes a chemical sampling device, the head module having: (i) a second processing circuit, a second memory circuit, and a second communications circuit; (ii) an optical sensor that is in communication with the second processing circuit; (iii) a first motorized transport device that physically moves the head module along the longitudinal member to a position that is controlled by at least one of the first processing circuit and the second processing circuit; and (d) a first accessory module having: (i) a first mounting leg that is installed along the longitudinal member at an unknown position; (ii) a first identification area at a predetermined location on the first accessory module that is visible when the first accessory module is installed on the longitudinal member, the first identification area exhibiting at least one of (A) a first predetermined color and (B) a first predetermined brightness; wherein: (e) the head module, under the control of at least one of the first processing circuit and the second processing circuit: (i) is moved by the first motorized transport device along the longitudinal member while the optical sensor detects electromagnetic energy comprising at least one of a color and an intensity of light, and (ii) if the optical sensor detects the at least one of the first predetermined color and the first predetermined brightness, then (iii) the optical sensor has detected the unknown position of the first accessory module along the longitudinal member, and the automated chemical sampling apparatus now has calibrated that unknown position.

In accordance with another aspect, a chemical sampling apparatus is provided, which comprises: (a) a main computer station, having a first processing circuit, a first memory circuit, and a first wireless communications circuit; (b) a head module that includes a chemical sampling device, the head module having a second processing circuit, a second memory circuit, and a second wireless communications circuit; (c) a first accessory module having a third processing circuit, a third memory circuit, and a third wireless communications circuit; (d) a power source that provides electrical energy to the main computer station, the head module, and the first accessory module; wherein: (e) the first processing circuit communicates first data signals with the second processing circuit using the first and second wireless communications circuits, and without the use of data cables between the main computer station and the head module; and (f) the first processing circuit communicates second data signals with the third processing circuit using the first and third wireless communications circuits, without the use of any data cable between the main computer station and the first accessory module.

In accordance with yet another aspect, a method for operating a chemical autosampler machine is provided, in which the method comprises the following steps: (a) providing a main computer station, having a first processing circuit, a first memory circuit, a first wireless communications circuit, a user command entry device, a display monitor, and a first power pathway; (b) providing a longitudinal member extending in a substantially horizontal direction and that is shaped and sized to receive at least one mounting leg of an accessory module; (c) providing a head module that includes a chemical sampling device, the head module having: (i) a second processing circuit, a second memory circuit, and a second wireless communications circuit; (ii) a first motorized transport device that physically moves the head module along the longitudinal member to a position that is controlled by at least one of the first processing circuit and the second processing circuit; and (iii) a second power pathway; (d) providing a first accessory module, the first accessory module having: (i) a third processing circuit, a third memory circuit, and a third wireless communications circuit; (ii) a first mounting leg; (iii) a third power pathway; (e) installing the first accessory module on the longitudinal member, using the first mounting leg; (f) providing at least one electrical power source, and connecting the first power pathway, the second power pathway, and the third power pathway to the at least one electrical power source; and (g) providing a main computer program that executes on the first processing circuit, the first processing circuit being configured: (i) to control data communications between the first processing circuit and the second processing circuit, without any data cable between the main computer station and the head module; (ii) to control data communications between the first processing circuit and the third processing circuit, without any data cable between the main computer station and the first accessory module; (iii) to control the first motorized transport device to allow the head module to perform chemical sampling functions; and (iv) to control the display monitor and to accept commands from the user command entry device, thereby allowing a human user to virtually select a second accessory module that will be physically added to the chemical autosampler machine, by: (A) installing a second accessory module on the longitudinal member, the second accessory module having a fourth processing circuit, a fourth memory circuit, and a fourth wireless communications circuit; (B) connecting a fourth power pathway to the second accessory module; and (C) commanding the main computer program to wirelessly communicate from the first communications circuit to the fourth wireless communications circuit, thereby controlling data communications between the first processing circuit and the fourth processing circuit, without any data cable between the main computer station and the second accessory module; thereby providing for quick expansion capability of the chemical autosampler machine, without requiring the addition of any data cable to the second accessory module.

Still other advantages will become apparent to those skilled in this art from the following description and drawings wherein there is described and shown a preferred embodiment in one of the best modes contemplated for carrying out the technology. As will be realized, the technology disclosed herein is capable of other different embodiments, and its several details are capable of modification in various, obvious aspects all without departing from its principles. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the technology disclosed herein, and together with the description and claims serve to explain the principles of the technology. In the drawings:

DETAILED DESCRIPTION

Figure 1:
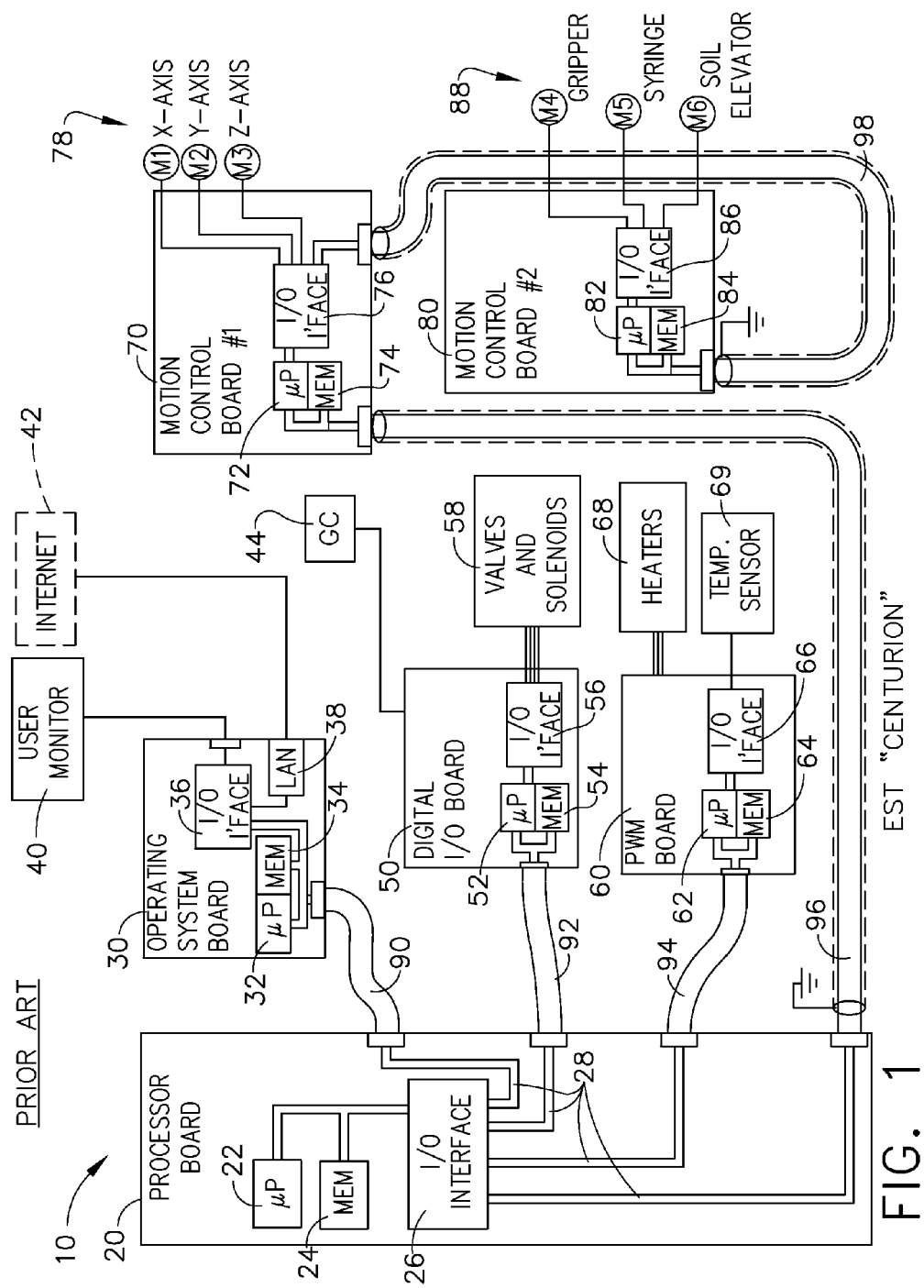
FIG. 1 is a block diagram of the major components of a prior art analytic autosampler sold by EST Analytical under the trademark "CENTURION."
Figure 2:
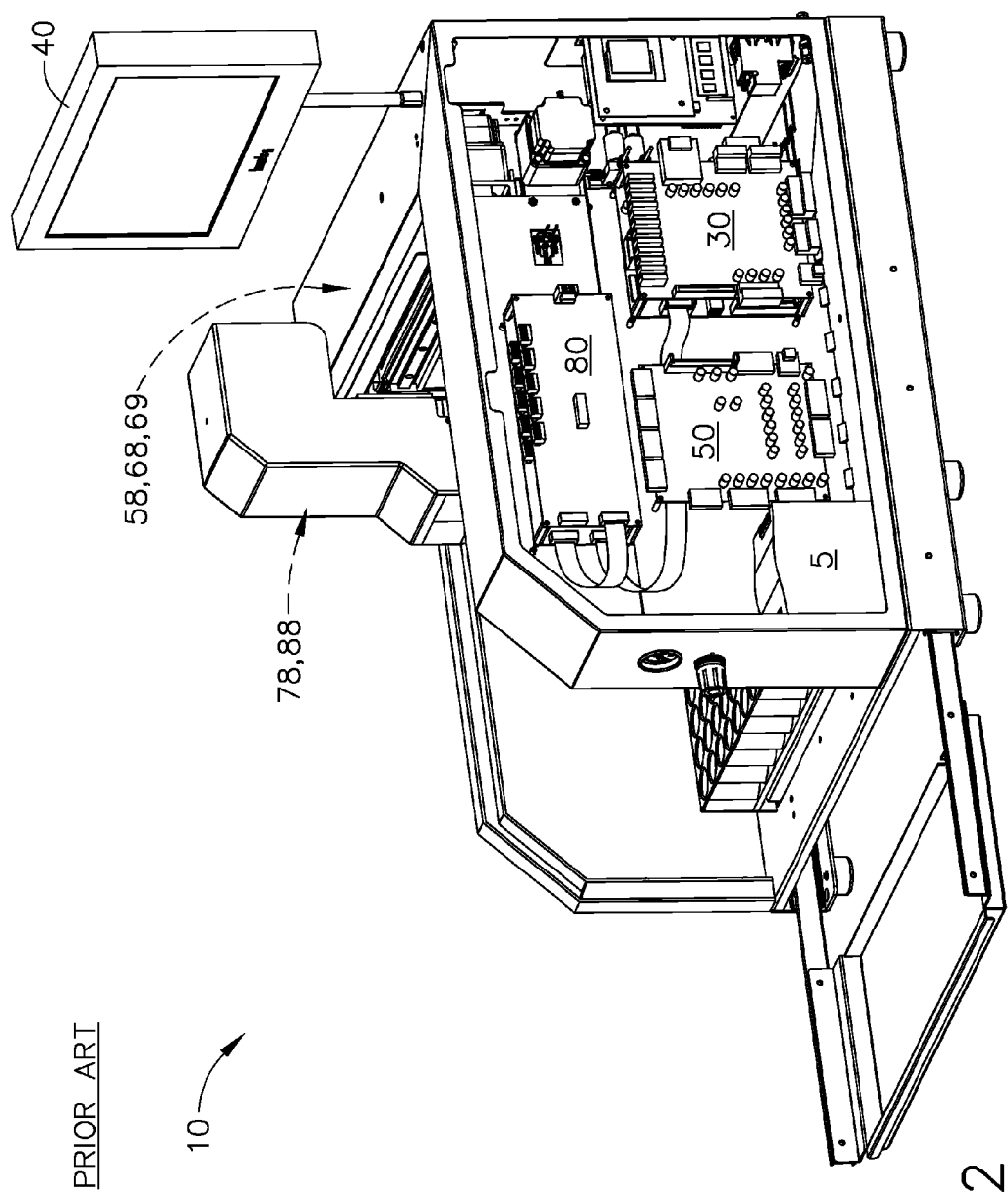
FIG. 2 is a perspective view of the prior art Centurion autosampler of FIG. 1, showing the entire unit with some of its covers open.
Figure 3:
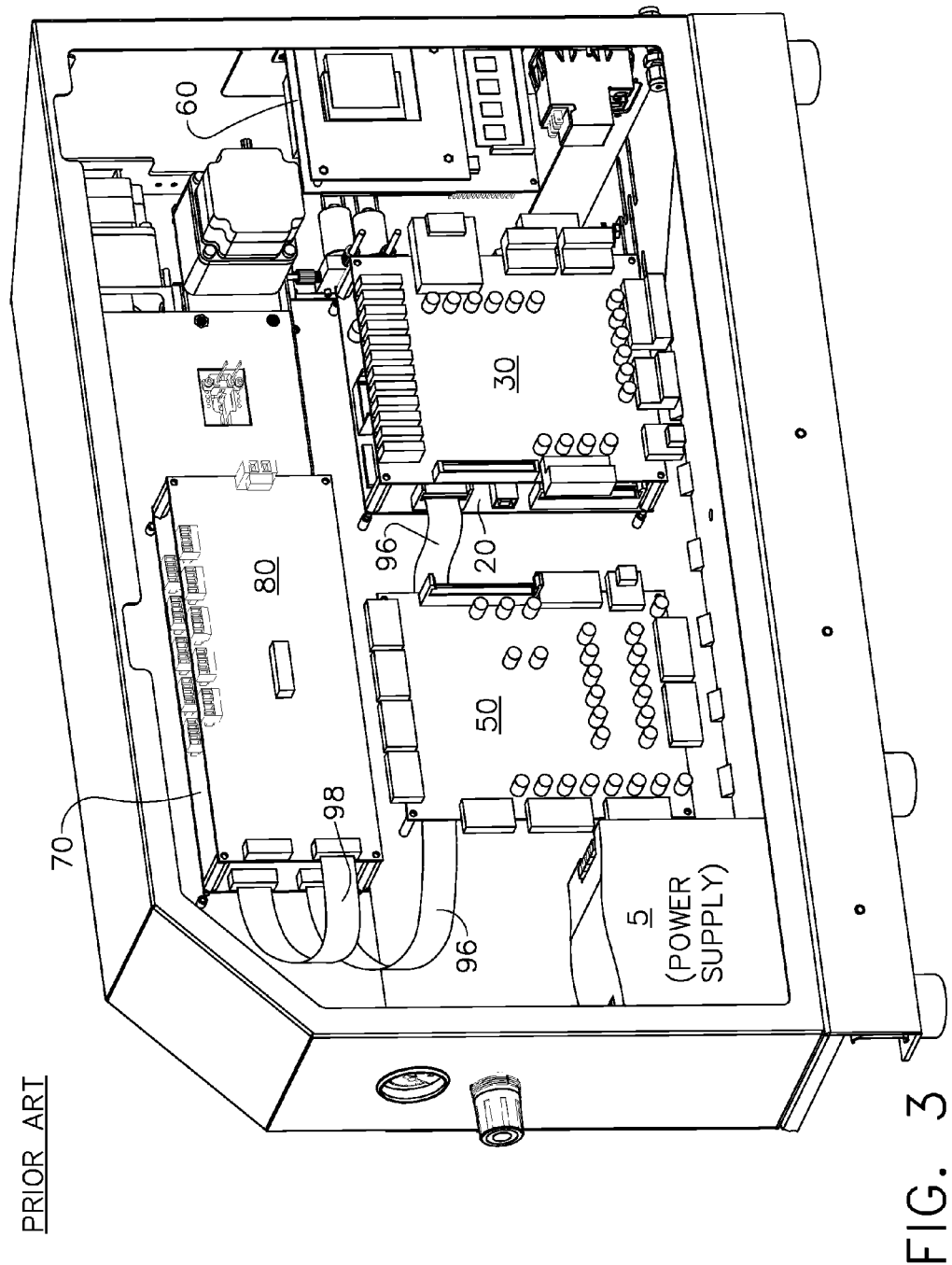
FIG. 3 is a perspective view of the electronics module of the prior art Centurion autosampler of FIG. 2.

Reference will now be made in detail to the present preferred embodiment, an example of which is illustrated in the accompanying drawings, wherein like numerals indicate the same elements throughout the views.

It is to be understood that the technology disclosed herein is not limited in its application to the details of construction and the arrangement of components set forth in the following description or illustrated in the drawings. The technology disclosed herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

The terms "first" and "second" preceding an element name, e.g., first inlet, second inlet, etc., are used for identification purposes to distinguish between similar or related elements, results or concepts, and are not intended to necessarily imply order, nor are the terms "first" and "second" intended to preclude the inclusion of additional similar or related elements, results or concepts, unless otherwise indicated.

In addition, it should be understood that embodiments disclosed herein include both hardware and electronic components or modules that, for purposes of discussion, may be illustrated and described as if the majority of the components were implemented solely in hardware.

However, one of ordinary skill in the art, and based on a reading of this detailed description, would recognize that, in at least one embodiment, the electronic based aspects of the technology disclosed herein may be implemented in software. As such, it should be noted that a plurality of hardware and software-based devices, as well as a plurality of different structural components may be utilized to implement the technology disclosed herein.

It will be understood that the term "circuit" as used herein can represent an actual electronic circuit, such as an integrated circuit chip (or a portion thereof), or it can represent a function that is performed by a processing device, such as a microprocessor or an ASIC that includes a logic state machine or another form of processing element (including a sequential processing device). A specific type of circuit could be an analog circuit or a digital circuit of some type, although such a circuit possibly could be implemented in software by a logic state machine or a sequential processor. In other words, if a processing circuit is used to perform a desired function used in the technology disclosed herein (such as a demodulation function), then there might not be a specific "circuit" that could be called a "demodulation circuit;" however, there would be a demodulation "function" that is performed by the software. All of these possibilities are contemplated by the inventors, and are within the principles of the technology when discussing a "circuit."

Figure 4:
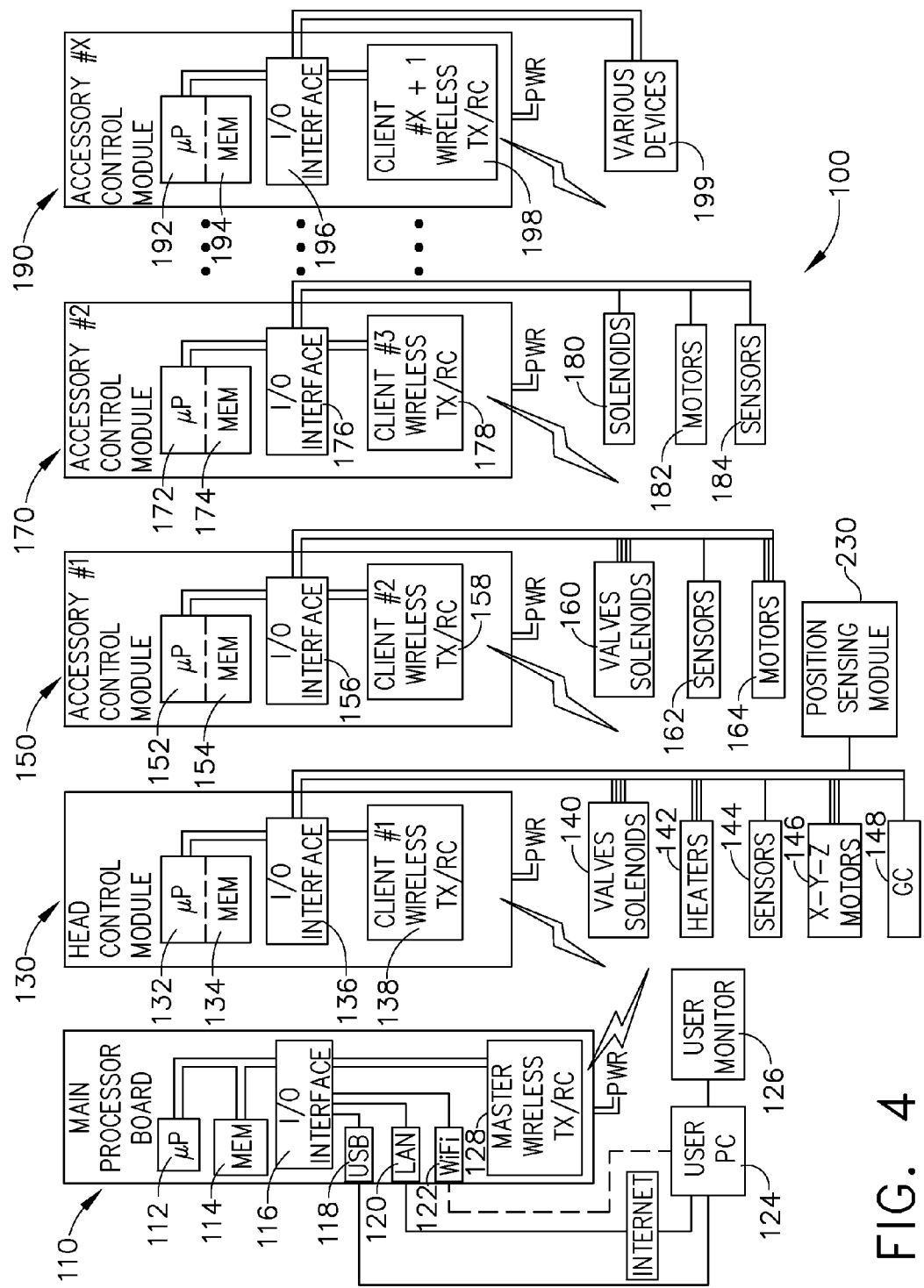
FIG. 4 is a block diagram of the major components of a chemical analytic autosampler, as constructed according to the principles of the technology disclosed herein.

Referring now to FIG. 4, the system block diagram showing the major electrical and electronic components of a new design EST Analytics chemical autosampler system are generally depicted by the reference numeral 100. There is a main processor board at 110, a head control module 130, and several accessory control modules. For the purposes of illustration of the capabilities of this new EST autosampler, FIG. 4 shows accessory control modules at 150, 170, and 190. The first accessory control module 150 could, for example, be for controlling an accessory module that includes an incubator and an agitator. Such a module would need valves and solenoids at 160, and motors at 164. It would typically require at least one sensor at 162 for measuring temperature, and perhaps other analog signals.

The second accessory control module 170 could, for example, be a "scale" module, used for weighing samples. Such a module would need at least one solenoid at 180, a motor 182, and a sensor at 184. This typically would be an analog sensor for measuring the mass of the sample being weighed, but there could be other sensors as well.

The accessory module 190 is simply illustrated to show the concept that the new EST Analytics autosampler can be expanded almost infinitely, at least with respect to the electronics that are involved. This will be explained in greater detail below.

On FIG. 4, the main processor board 110 includes a processing circuit 112, a memory circuit 114, an input/output (I/O) interface circuit 116, and several ports 118, 120, and 122. These ports are for communicating data to a user personal computer at 124. Usually only one of these three ports would be used by a particular user, but this gives that user some flexibility: there is a USB port 118, and Ethernet LAN port 120, and a WiFi wireless port at 122. The user would select whichever of those ports is desired for his particular personal computer. This user would typically also supply a monitor at 126 that is connected to PC 124.

The main processor board 110 must communicate with the other modules in the autosampler system. Instead of using several different multi-conductor flat cables, as in the EST Centurion autosampler, the new design autosampler uses wireless communications for talking to each of the other modules. In a preferred mode of communication, the main processor board includes a "master" wireless transmitter and receiver circuit 128, which is based on the M2M protocol that is used in many industrial processes. This wireless communications protocol allows the other modules in the autosampler system to be positioned at virtually any physical location in the autosampler, as per the user's desire. At the same time, the new autosampler system is also easily expandable without the need for adding any more signal (or "data") cables. All one has to do is provide a power pathway (such as a power cord or power cable) to each module, and that module will then be able to communicate with the main processor board by way of that wireless communications protocol. On FIG. 4, the power pathways are generally designated by the acronym "PWR," as shown being connected into each of the electronic modules.

On FIG. 4, there is head control module 130 that includes a processing circuit 132, a memory circuit 134, an I/O interface circuit 136, and a wireless transmitter and receiver circuit 138. In the M2M protocol, each of the non-master communications nodes are known as "clients." Therefore, on FIG. 4, the head control module is referred to as "CLIENT #1" at the wireless transmitter/receiver 138.

The head control module 130 in the new autosampler includes virtually all the same valves and solenoids at 140, heaters at 142, sensors at 144, stepper motors at 146, and a GC at 148 that are found in the prior art EST Centurion autosampler that was illustrated on FIG. 1. As will be seen in the later figures, the head module is a physically large device, and that is mainly because of all the included mechanical components rather than the electronic ones. And one nice attribute of this new autosampler design is that the heaters can draw their required current for operating properly, and there are no shielded cables required inside the head module itself. By use of the wireless communications design, the electrical noise immunity has been greatly increased, as compared to older autosampler designs.

In the autosampler illustrated in FIG. 4, autosampler 100 also has some accessory modules. Each accessory module will be positioned along a mounting rail 218 that will be more fully described below in reference to some of the illustrations provided herein. On this electrical block diagram, only the "smart modules" are depicted, which are modules that have electronics. Starting with an accessory #1 control module, generally designated by the reference numeral 150, this module has a processing circuit 152, a memory circuit 154, an I/O interface circuit 156, and a wireless transmitter and receiver circuit 158. In this figure, the wireless transmitter/receiver module 158 is designated "CLIENT #2." Because of this wireless communications device 158, the accessory control module 150 can communicate with both the head control module 130 and the main processor board 110, as required by the overall autosampler system requirements. In this example of FIG. 4, the accessory control module 150 has a set of valves and solenoids at 160, sensors at 162, and motors at 164. An accessory module of this configuration could be an incubator/agitator module. The motors 164 would include a motor for vibrating the chemical sample vial inside the container of the module, and there could be a temperature sensor, as well as a heater element that makes up the incubator function.

Another accessory control module is depicted at 170, and this second accessory control module includes a processing circuit 172, a memory circuit 174, an I/O interface circuit 176 and a third client wireless transmitter and receiver circuit 178. This wireless node is referred to as the "CLIENT #3" communications node in the system 100 of FIG. 4. In this example, the second accessory control module 170 includes a solenoid 180, a motor 182, and a sensor 184. This could be a scale that is used to weigh certain chemical samples.

The autosampler 100 that is depicted on FIG. 4 and comprising the technology disclosed herein, can be easily expandable simply by adding additional accessory modules to the mounting rail. This is diagrammatically depicted on FIG. 4 by an accessory control module #X, depicted at the reference numeral 190. Control module 190 includes a processing circuit 192, a memory circuit 194, an I/O interface circuit 196, and a client wireless transmitter and receiver circuit 198. On FIG. 4, the wireless transmitter/receiver node is referred to as the "CLIENT #X+1" node, for the accessory #X control module. Such a module can have various types of input and output devices, generally depicted by the reference numeral 199, that are connected to the I/O interface circuit 196.

The expansion capability of the autosampler depicted on FIG. 4 is such that any number of accessory control modules can be added so long as there is physical room on the rail. And moreover, the physical rail can be lengthened to any desired length for a particular customer's installation, so virtually any number of accessories can be mounted to that rail. No flat cables need to be added to the system, and there would be no space limitations inside a control cabinet; the only space limitation is the length of the rail itself (which will become apparent in the successive views). The data signals can be transmitted and received between the main processor board 110 and the head control module 130 with respect to any of the accessory control modules. In other words, the master wireless node 128 can communicate with the client #1 wireless node 138, and either or both of these wireless nodes can communicate with any of the other accessory wireless nodes, on FIG. 4 depicted at 158, 178, and 198. The point here is that additional accessory modules not actually illustrated on FIG. 4 can be installed between accessory #2 and accessory #X, and all of the wireless transmitter and receiver circuits will be able to communicate with the head control module and the main processor board. The only extra hardware that is required is a power supply cable that can be plugged into each one of the accessory modules, as needed. It must be noted that there will be accessories that are "dumb" devices, and have no electronics at all; such modules will not need any type of wireless transmitters or receivers.

Figure 5:
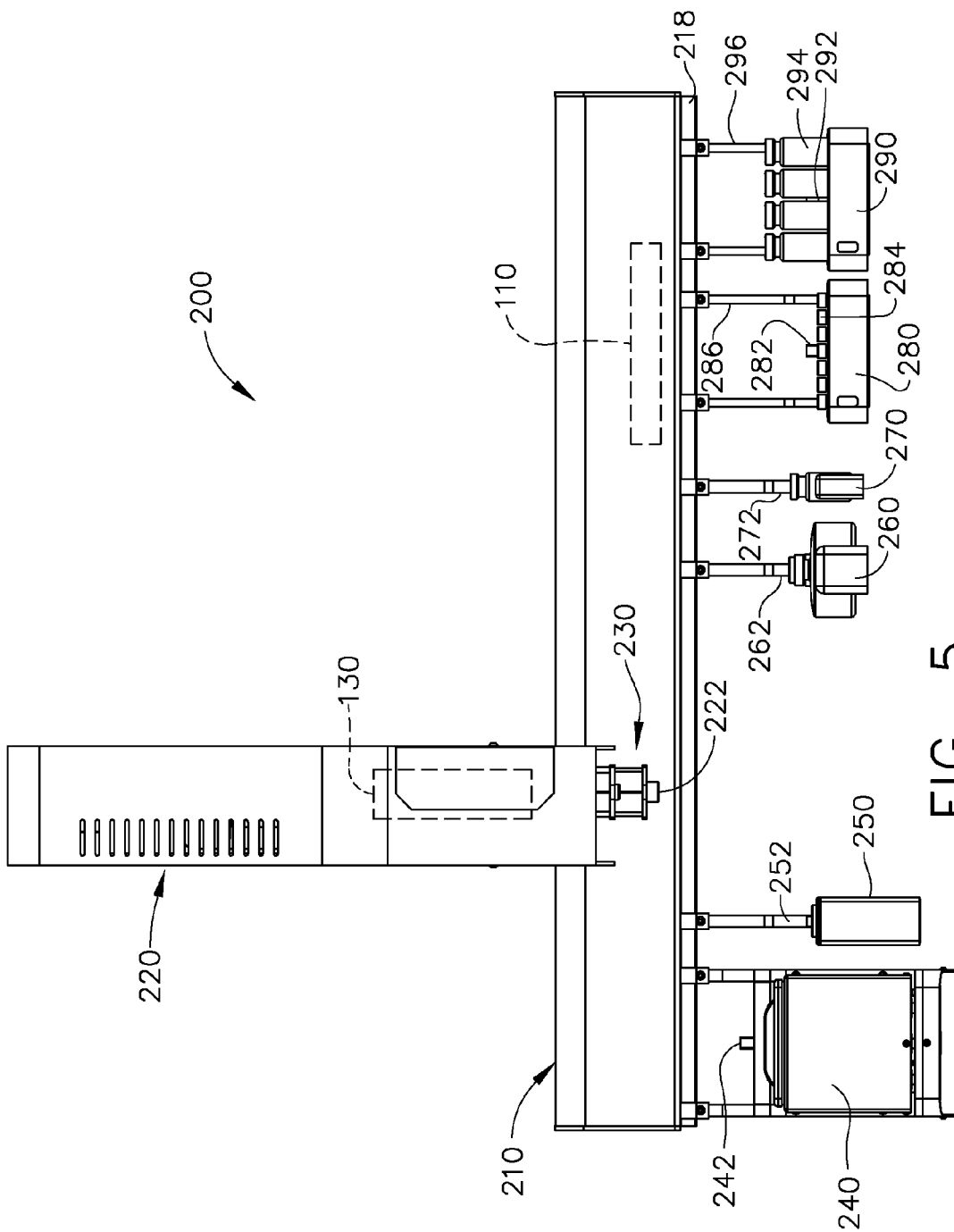
FIG. 5 is a front elevational view of the autosampler depicted in FIG. 4.
Figure 6:
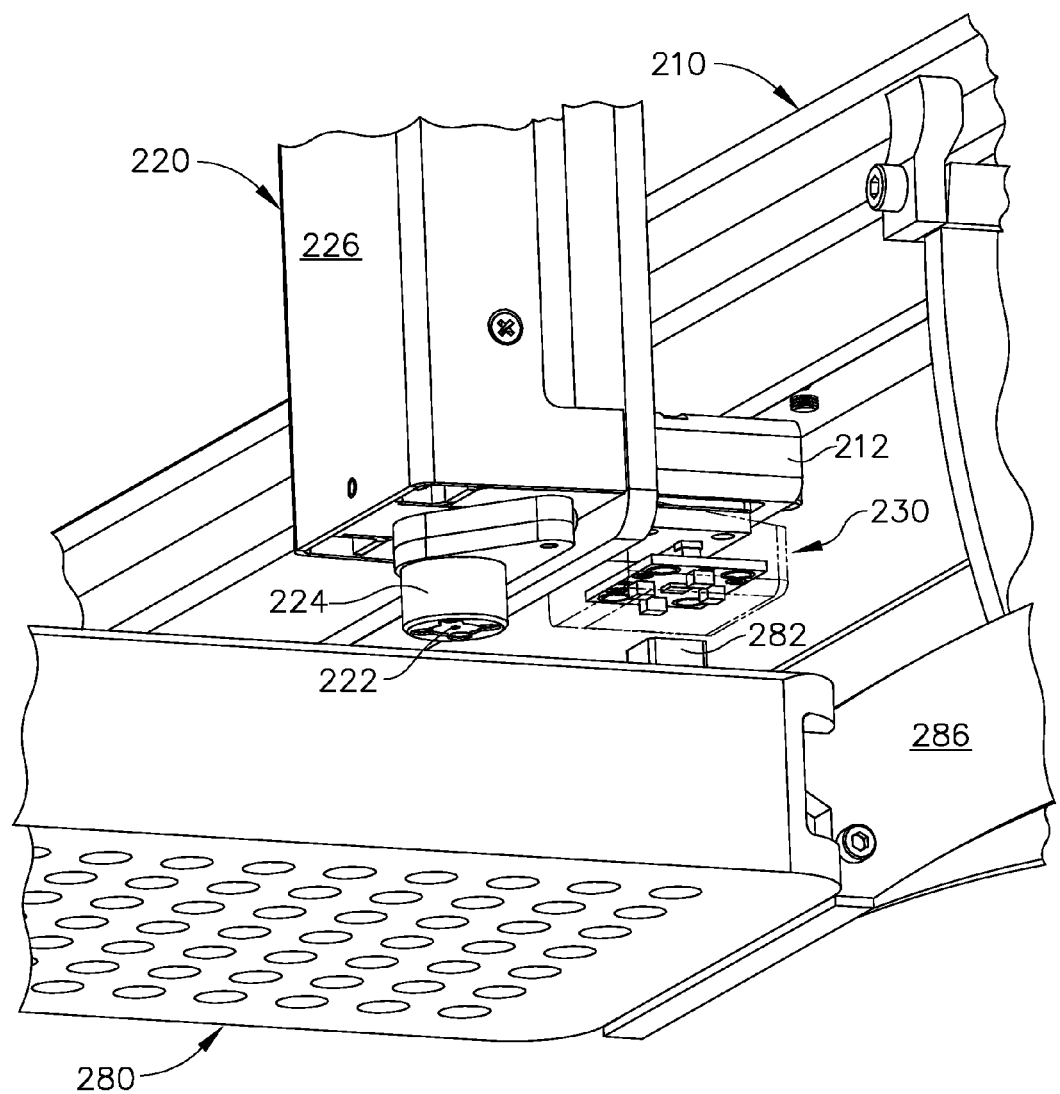
FIG. 6 is a perspective view taken from the front-right quarter of the autosampler of FIG. 5, showing some of the details of the head module.

Referring now to FIG. 5, an entire autosampler unit of the new design is illustrated, and is generally designated by the reference numeral 200. The main body of the unit 200 is described as a rail module, and is generally depicted by the reference numeral 210. The device 200 has a head module, generally depicted by the reference numeral 220. This head module includes a head control module electronic circuit 130, which was described in reference to FIG. 4. In addition, head module 220 also includes a color sensor module 230, which will be described in greater detail below. The head module also has a fitting for holding a syringe at 222, which will also be illustrated in more detail below. The rail module 210 includes a physical mounting rail at 218, and also includes the main processor board 110, which was described above in relation to FIG. 4. Mounted to the physical mounting rail 218 are several different modules, some of which are "smart" modules and some of which are "dumb" modules.

As illustrated on FIG. 5, the module to the left is illustrated as an incubator/agitator module also known as a "head space module," and generally designated by the reference numeral 240. This module 240 has an identification marker 242, which will be described in greater detail below. The next module to the right on FIG. 5 is illustrated as an "SPME conditioner" which includes a heater and thermocouple. This module is generally designated by the reference numeral 250, and has an identification marker 252. The next module illustrated on FIG. 5 is a wash station for 100 ml vials, generally designated by the reference numeral 260. Module 260 includes an identification marker 262. The next module is a smaller wash station, one that handles ten (10) ml vials, generally designated by the reference numeral 270. Module 270 includes an identification marker 272.

The next module to the right on FIG. 5 is a tray that holds multiple 2 ml vials, and is generally designated by the reference numeral 280. Tray 280 includes an identification marker 282. The last module on FIG. 5, all the way to the right on this view, is another tray that holds larger vials, in this case, 20 ml vials, and is generally designated by the reference numeral 290. Tray 290 includes an identification marker 292.

A few additional details about FIG. 5: there are several small vials illustrated as being held by the 2 ml vial holder 280, and one of those vials is designated by the reference numeral 284. The module itself has two mounting arms (or legs) that attach the module to the rail 218, one of which is numbered 286. The larger tray 290 shows multiple larger 20 ml vials, one of which is designated by the reference numeral 294. The tray 290 also has two mounting arms (or legs) one of which is designated 296. These mounting arms/legs physically attach the modules to the mounting rail 218.

Many other types of modules can be mounted to the autosampler depicted in FIG. 5. For example, there can be a heater module, a gripper module, a motion control module, a scale module that weighs chemical samples, a solid material module that samples soil or other types of solid materials, and also a plumbing module with flow control devices. Additional types of modules can of course by added to the system, as needed in the future. Some of these modules will be "smart" modules, and in that situation each one will include an M2M wireless transmitter and receiver for communicating data signals to and from the main processor board and/or the head control module that are illustrated on FIG. 4. In that way, each smart module will be in communication with the overall autosampler, and will be provided with instructions as needed, and will send back data as needed.

Figure 7:
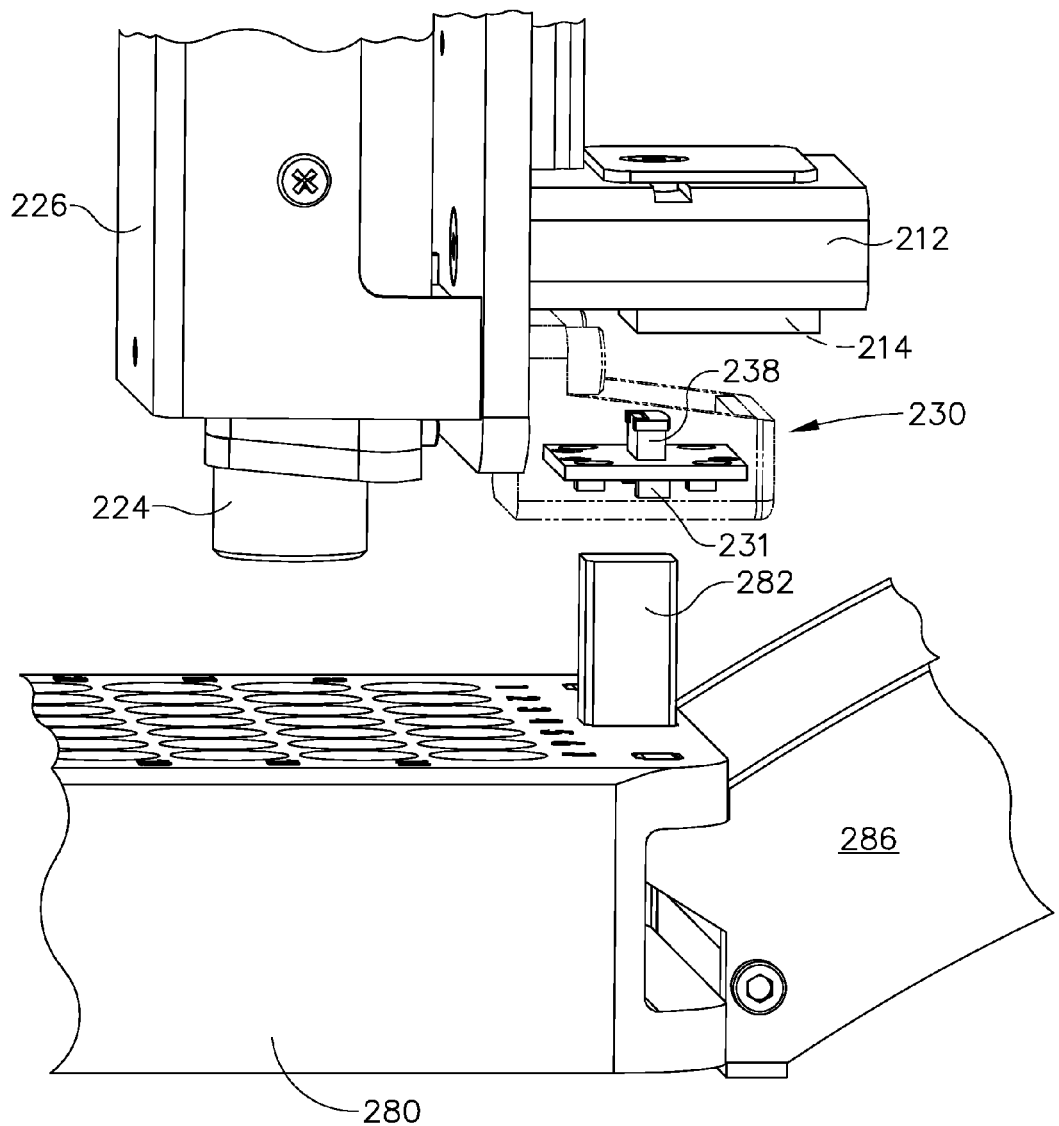
FIG. 7 is a perspective view taken almost directly from the right-hand side of the autosampler of FIG. 5, showing some of the details of the optical sensor and the identification marker of an accessory.
Figure 8:
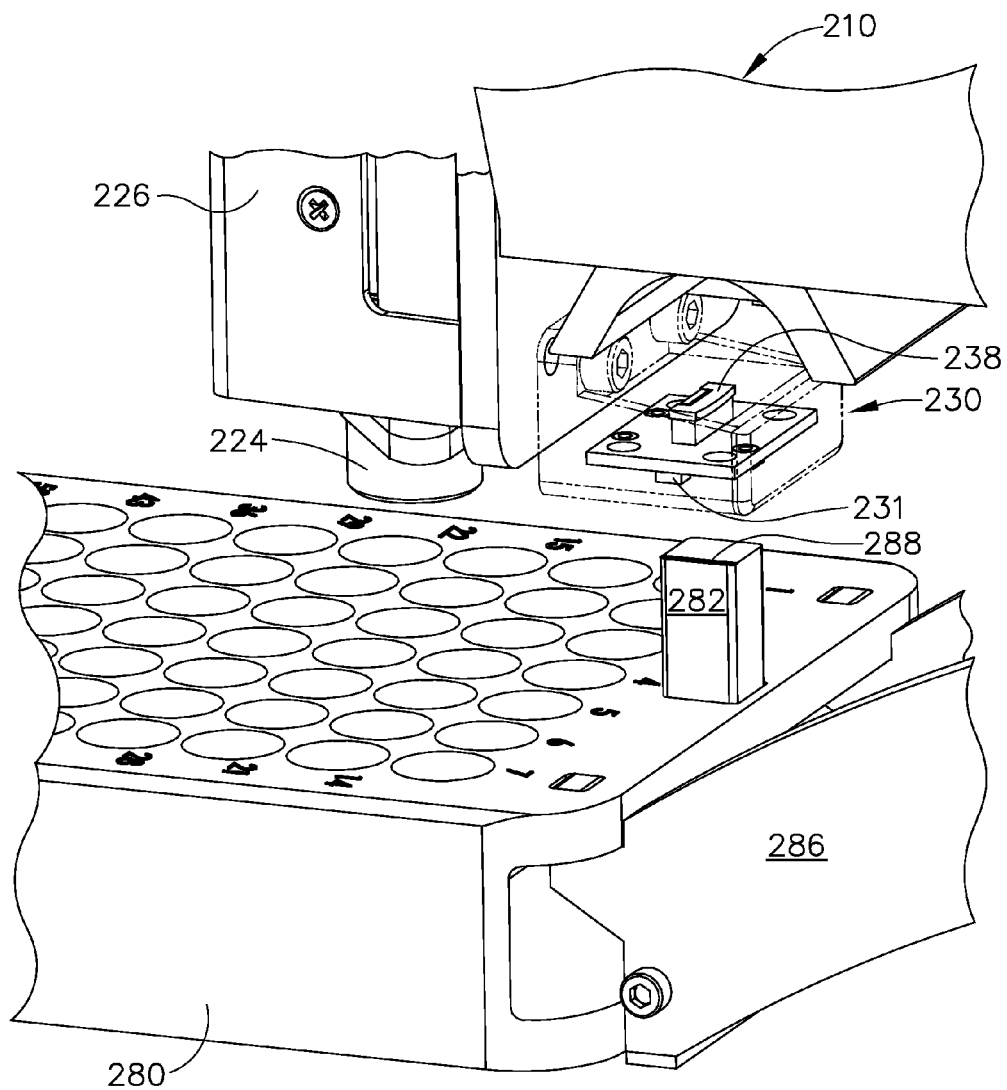
FIG. 8 is a perspective view taken from the right, rear quarter of the autosampler of FIG. 5, again showing the details of the optical sensor and identification marker of an accessory.
Figure 9:
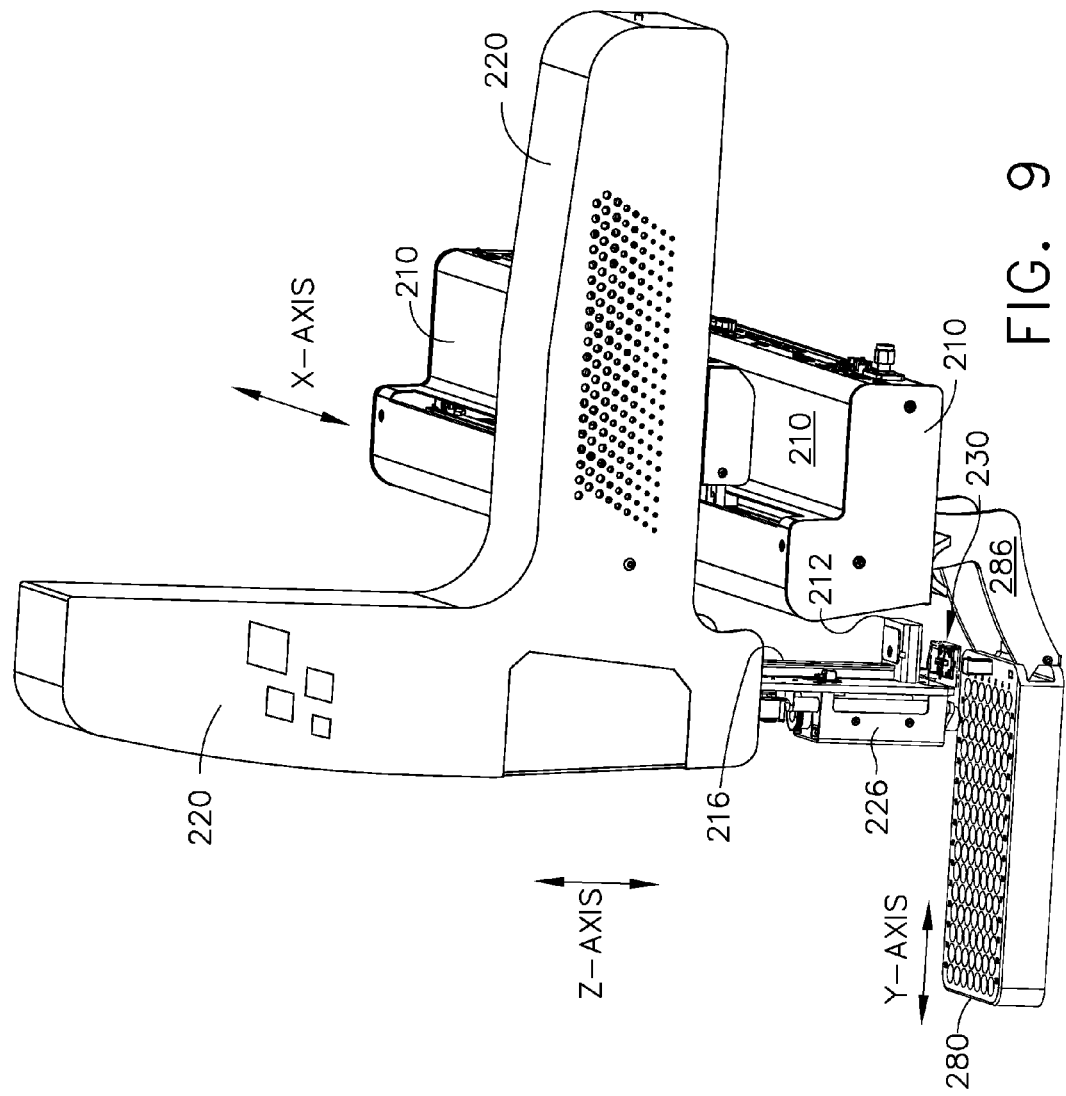
FIG. 9 is a perspective view taken from above and from the right-hand side of the autosampler of FIG. 5, and shows the three different axes of motion of the head module.

Referring now to FIGS. 6-11, several close-up views are provided of the bottom portion of the head module 220, and an overall view of the entire instrument is provided on FIG. 9, also showing the orientation of the head module with respect to the rail module. On FIG. 6, the bottom areas of one of the multiple vial trays 280 are illustrated, and showing a portion of the mounting leg 286. The bottom of the head module 220 is illustrated, showing a syringe cover 226, a needle guide 224, and an opening for the syringe to pass through at 222. Just behind this portion of the head module is a color sensor module 230, and the identification marker 282 for that particular tray 280. Above the color sensor module is a Z-drive belt clamp block 212.

FIG. 7 shows essentially the same equipment from a different perspective angle, and at this angle, the Z-drive belt cover can be seen at 214. Inside the color sensor module 230 is a set of light emitting diodes, and the "leading edge" LED is visible, designated by the reference numeral 231. Above the circuit board for the color sensor module is a connector 238. This view of FIG. 7 provides a relative idea of the proximity of the color sensor module 230 with respect to the identification marker 282, as the sensor module 230 is attempting to identify the precise location of that identification marker 282.

FIG. 8 also provides a similar view from yet a different perspective angle, this time showing the sample tray 280 from above. The overall shape of the identification marker 282 can be seen in this view, which has a square profile on its upper surface. The shape of the ID marker can be of any desired design; however for the purposes of the autosampler, the leading and trailing edges preferably are substantially straight lines. One of the edges can have a visually different color than the remainder of the upper surface of the identification marker, if desired. On FIG. 8, such a colored edge is illustrated at 288. The color light sensor module 230 can discriminate between the edge color at 288 and the other color of the remainder of the top surface of marker 282. Position sensing for the accessory module can thereby be based upon that edge color.

FIG. 9 shows the autosampler from yet another perspective angle, this time almost exactly from the right end. The entire autosampler is depicted in FIG. 9, and shows the relative positions of the rail module 210 and the head module 220. The sample vial tray 280 can be seen extending to the left in this view, as it hangs off of its mounting legs 286. In this view a portion of the head module known as the "Z-rail" is visible at 216. The bottom portion of the head module moves up and down along a Z-AXIS, which means that the syringe itself moves up and down, as well as the color sensor module 230. The entire head module is capable of moving in two other axes of motion as well, including a Y-AXIS that allows the syringe to move left and right (in the view of FIG. 9) to sample a different row of vials. The head module can also move in and out (in this view of FIG. 9) along the X-AXIS, which again allows the syringe to move back and forth along the X-AXIS to sample a different column of vials. FIG. 9 provides a clear illustration of the three-axes of linear motion that can be achieved by the head module 220 with respect to the rail module 210.

Figure 10:
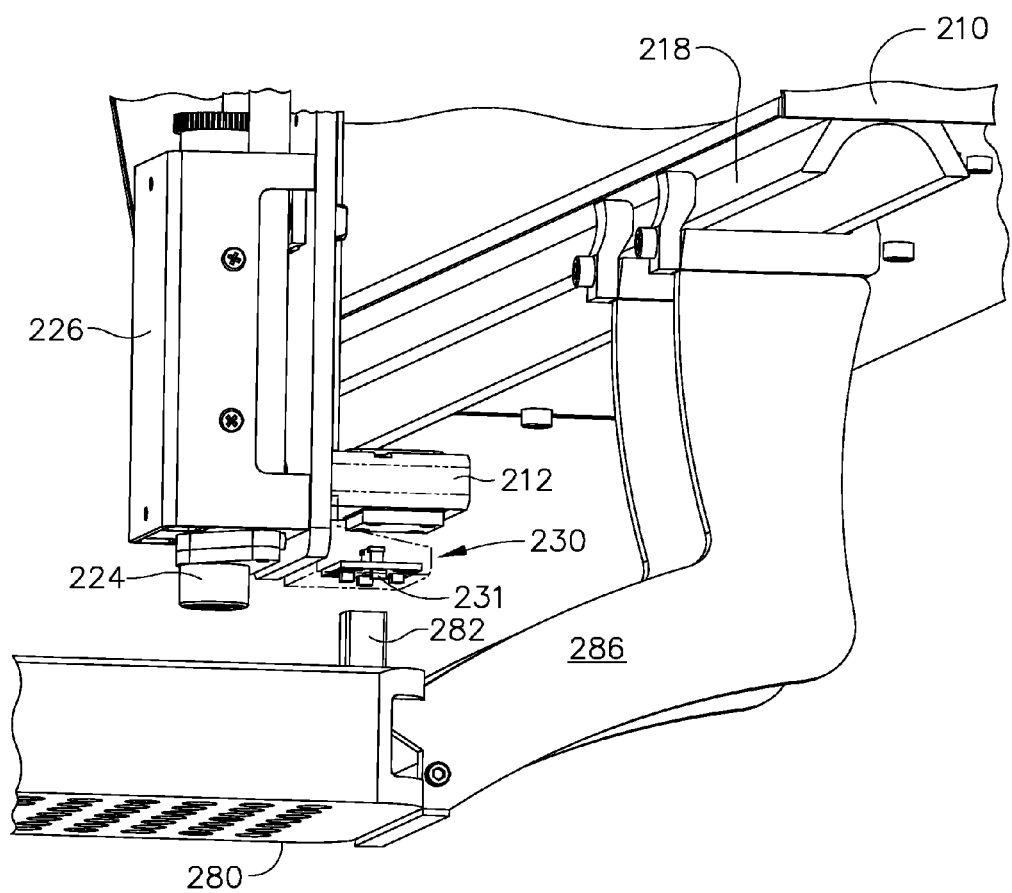
FIG. 10 is a perspective view from the right-hand side and slightly below the mounting rail of the autosampler of FIG. 5, showing details of the optical sensor and identification marker of an accessory.
Figure 11:
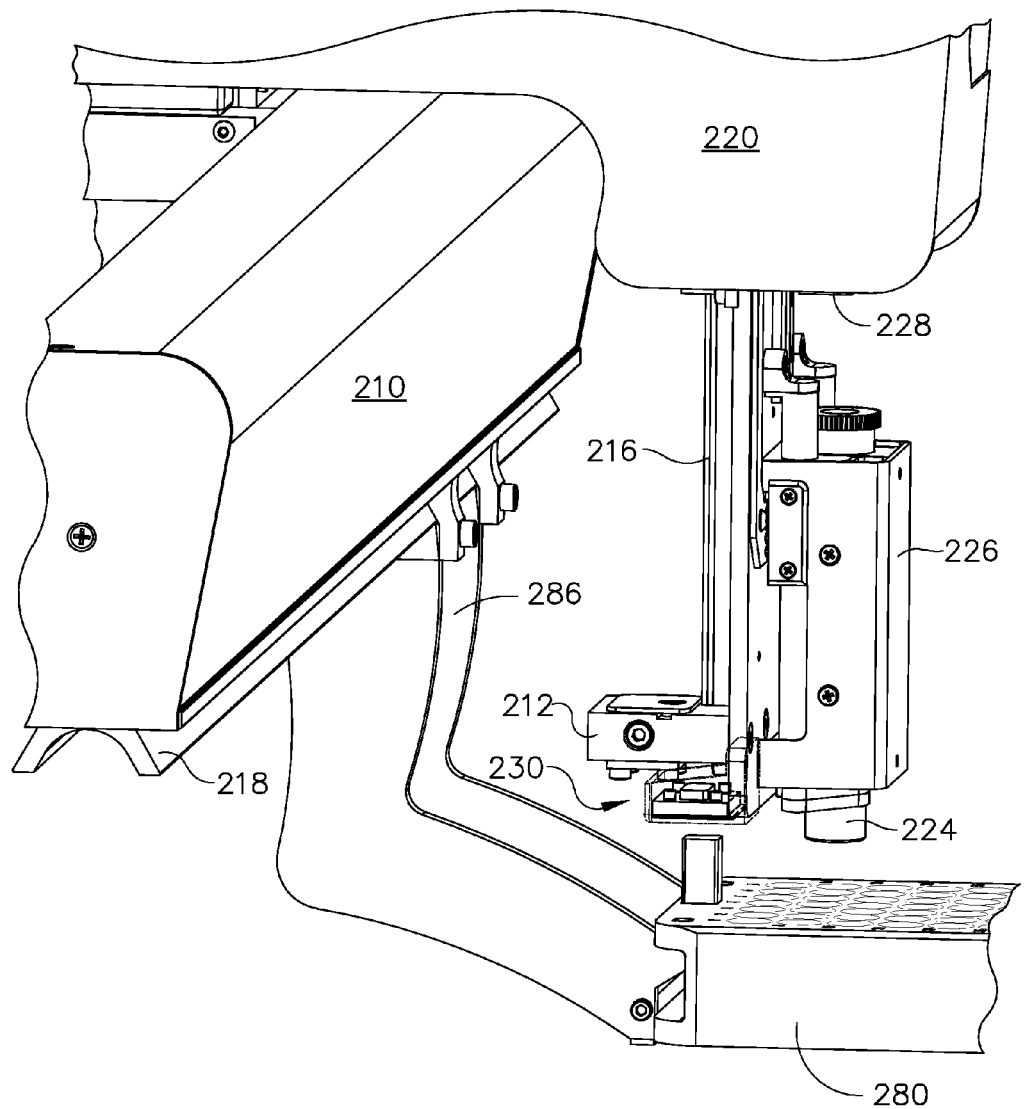
FIG. 11 is a perspective view taken from the left-hand side and from above, of the autosampler of FIG. 5, showing details of the head module and an accessory.

FIGS. 10 and 11 show some more interesting views from nearly straight on along the X-AXIS. FIG. 10 shows the device from the right end, while FIG. 11 shows the device from the left end (with respect to FIG. 5). Both views show the physical mounting rail 218 and show some of the details as to how the mounting leg 286 attaches to that rail 218. All of the various modules have mounting legs such as the one illustrated at 286, and they all can mount to the longitudinal rail 218 in the same manner.

It will be understood that the exact mounting location is strictly up to the user of the autosampler, and once each accessory is mounted to the longitudinal rail 218, the head module will be used to find the physical position of each of those accessories. That is one of the main purposes of having the identification markers 282, and their use will be described in greater below.

It will be understood that the longitudinal rail 218 is merely one structural member of the much larger rail module 210. Rail module 210 contains many electronic parts, control wiring, and power wiring that are not visible in these views. In a similar manner, the head module 220 contains many electrical and electronic components, as well as control wiring and power wiring, that are not seen in these views. Certain of the bottom components of the head module 220 are visible, and for example in FIG. 11, the Z-rail is visible at 216, the syringe subassembly cover is visible at 226, and the syringe plunger holder is partially visible at 228.

Figure 12:
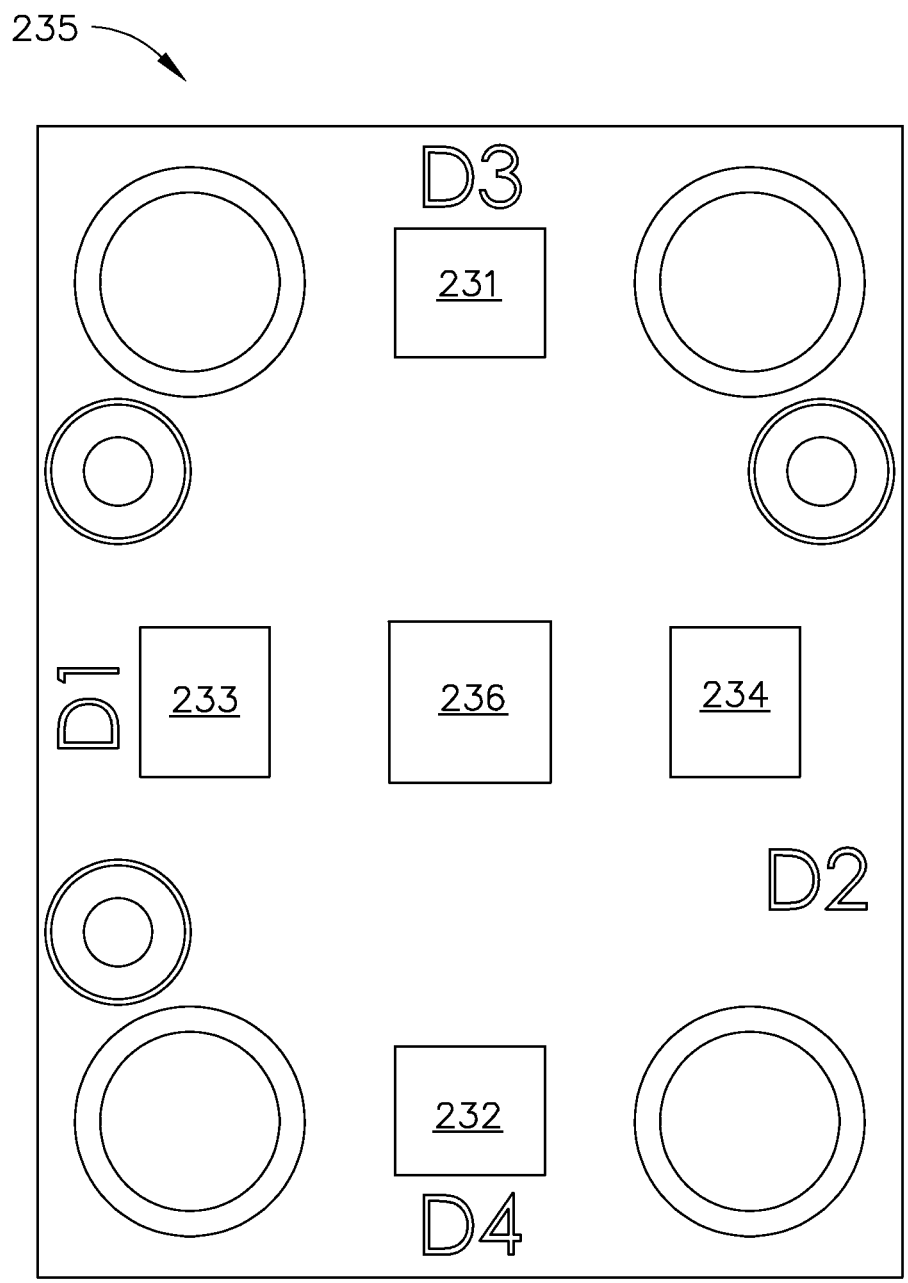
FIG. 12 is an elevational view of the optical sensor printed circuit board, used in the autosampler of FIG. 5.

Referring now to FIG. 12, the color sensor module 230 includes a printed circuit board that mounts several optoelectronic components. There is an optical sensor in the middle at 236, and there are four LEDs 231-234. These components are physically mounted to the circuit board, which is generally designated by the reference numeral 235. The LEDs are also depicted as D1, D2, D3, and D4, which are their designations on the circuit board itself. The LED 231 is designated as the "leading edge" diode, which means that, as the head module 220 traverses the rail module 210 moving to the right in the view of FIG. 5, this LED 231 will be the first one of the four LEDs to illuminate one of the identification markers on one of the accessory modules. By the same token, the LED 232 is referred to as "trailing edge" diode, because it will be the last LED to illuminate one of the identification markers, as the head module 220 traverses the mounting rail module 210 moving to the right on FIG. 5. Of course, the head module 220 also traverses to the left, as needed. In that situation, the designations "leading edge" and "trailing edge" would be reversed, with respect to any descriptions identifying how the LEDs are used. The LED 234 is the closest one to the rail module 210, while the LED 233 is the closest one to where a human user would normally stand when using the autosampler 100.

In the illustrated embodiment, each of the LEDs 231-234 produces substantially white light, and therefore, can be used to successfully illuminate identification markers of virtually any color that is desired for the various types of accessory modules. For example, all the markers themselves could be white, and the head module 220 will be able to successfully traverse the rail module 210 from left to right, and one at a time, come upon each of identification markers (such as the markers 242, 252, 262, 272, 282, and 292 illustrated on FIG. 5), and find the physical position of each of those markers along the rail 210. Once that has occurred, the head module 220 will be able to physically negotiate anywhere along the various types of modules attached to the physical mounting rail 218, because each of the modules themselves have known physical dimensions, and the head module 220 will have programming and data stored in its memory circuits to know how to physically interact with those modules. This includes the "dumb" modules, such as the multiple vial tray holders. This is explicitly one of the purposes of using the identification markers so as to find the substantially precise locations along the X-Y axes compared to the mounting rail 218, and then the syringe attached to the head module 220 will be able to successfully be positioned each of the sample vials as needed.

The distance tolerance allowed for interactions between the head module and the accessory modules is primarily dependent on the physical sizes involved with the hardware of each type of accessory. If the accessory is a tray that holds multiple sample vials, then the size of the vials is likely to be the limiting factor. For example, a tray holding 2 ml vials needs more accuracy in sampling syringe movements than a tray holding 20 ml vials, because the openings of the 2 ml vials have a much smaller inside diameter than the 20 ml vial openings. On the other hand, from a design engineering standpoint, it makes sense to design the entire autosampler system with an overall ruling tolerance, and make that tolerance the standard for all accessory modules throughout the entire system.

The smallest distance that can be moved by the head module is a single step of one of its three linear axes stepper motors, so the ruling tolerance cannot be allowed to be less than that distance. Fortunately, that distance (of a single step or pulse of the stepper motors) is quite small. In one mode of the new design autosampler, a preferred tolerance for positioning the head module with respect to identifying the physical locations of the accessories mounted to the rail module is about +/-_____ inches (or +/-_____ mm) Of course, a different tolerance could be selected by the system designer, if desired. This is merely one example for what can be referred to as a "substantially precise location" of a position along the rail on the autosampler system.

A further refinement of this system is to use a specific color on the identification markers for specific types of accessory modules. For example, the 2 ml vial trays could have a color red on their identification marker, while the larger 20 ml vial trays could have the color blue on their identification markers. It will be understood that such colors on the identification markers could be applied to the entire upper surface of the marker, or probably more useful, could be applied to just one of the edges of the marker, such as its leading edge or its trailing edge.

In addition to the above, with the four different LEDs that are included in the color sensor module 230, additional refinements in position sensing can be utilized. For example, only the leading edge LED 231 could be illuminated for certain types of position detecting, or instead, only the trailing edge LED 232 could be illuminated. Furthermore, regardless of which LEDs or LED combinations are used for illumination, the sensor itself at 236 could be looking for either a leading edge or a trailing edge of the identification markers of the accessories. Not only that, but the color optical sensor itself has the ability to detect RGB data, and therefore, that sensor module could be looking for a predetermined relatively small range of RGB data, which could be used to identify certain specific types of accessory modules. This system has great flexibility, as can be imagined, especially when using color RGB data for identification purposes.

Finally, as generally discussed in the above description, since there are no shielded flat cables anywhere in the autosampler system 100, this wireless design has a much greater noise immunity capacity than the older hard-wired design of the EST Centurion autosampler, particularly by eliminating multi-conductor flat cables for carrying data signals. While the heaters and stepper motors of the new design autosampler 100 are probably just as noisy than those used in the prior art EST Centurion autosampler 10, the overall electronic packaging and methodology used in communicating the data signals has improved the EMI rejection capabilities in the newer system. The optical sensing capabilities described above are also relatively immune to the EMI interference, since the actual colors of light and reflective surfaces of the identification markers will not be affected in the least by inductive or capacitive electromagnetic noise of any degree. So long as good practices are observed in designing the printed circuit boards for the various autosampler control modules and the main processor board, the EMI rejection characteristics of the new autosampler system 100 will be much superior.

Figure 13:
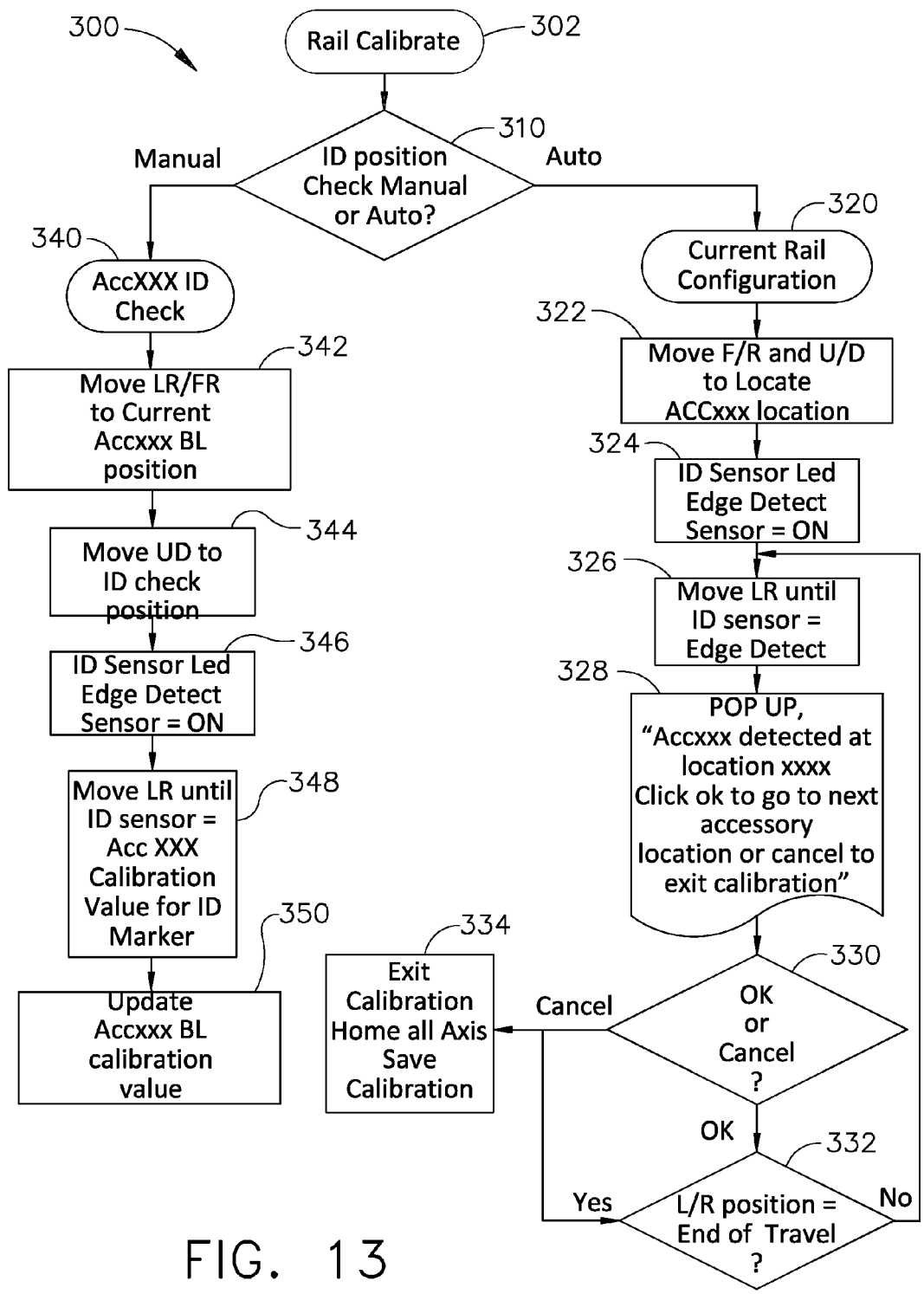
FIG. 13 is a flow chart of the steps performed by a "rail calibrate" routine used by the autosampler of FIG. 5.

The analytical chemical autosampler 10 described above includes an automatic position calibration procedure, and a flow chart is provided as FIG. 13. This routine is sometimes referred to as the "rail calibrate" routine, and the flow chart is generally designated by the reference numeral 300. Beginning at an initialization step 302, the logic flow is directed to a decision step 310 at which the user is allowed to select either a manual or automatic mode for checking the position of the various accessory modules that are mounted to the main rail 210. If the user selects the automatic routine, the logic flow is directed to a step 320 at which the operational software determines what the current rail configuration should be. Before step 320 is reached, the user should have mounted the appropriate accessories—or perhaps mounted a new accessory— onto the rail module, so as to install that accessory (or accessories) into the overall system.

Part of the main operational routine performed by the main processing board 110 is to provide a user interface software program that will be installed on the user's PC 124 (see FIG. 4). Using the monitor 126, the user has a graphical user interface (e.g., Windows sold by Microsoft) to monitor and enter commands to the overall system, via one of the data links from the user PC 124 to the I/O interface 116 of the main processor board 110. Before proceeding with the rail calibrate routine 300, the user will execute a portion of the main processing executable program to display a diagrammatic view of the overall analytical system 100, which shows a physical representation of the rail, and its various accessory module that can be, or are already have been, mounted to the main rail 210. To add a new accessory module, the user will click on one of the accessories that are depicted on the user monitor's viewing screen, and will drag that particular accessory module to the pictorial image of the actual rail, and then release. This will add the accessory to the system virtually, but now that accessory must be actually located with regard to its physical position on the rail.

Referring back to FIG. 13, the current rail configuration at step 320 will be determined, and the control software will command the head module 220 to move to the predicted physical position of the first accessory mounted to the rail. The control software running on the main processor board 110 virtually knows what types of accessory modules have been mounted to the rail, using the procedure described just above, and the transport motors of the head module 220 will now be controlled in an appropriate manner. The X-axis transport motor is also referred to as the left/right (or L/R) stepper motor, which brings the head module 220 to the appropriate predicted physical position along the longitudinal rail 218. Once at that predicted position, the head module will control its syringe subassembly, which also has the optical sensor subassembly (the color sensor module 230) attached thereto, to move the optical sensor 236 to the appropriate more precise position for positively detecting the identification marker of that particular accessory, at a step 322.

At step 322 on FIG. 13, the main processor executable program will instruct the head module to move the forward/reverse (F/R) transport motor and also the up/down (U/D) transport motor into the appropriate (predicted) positions so they are within close proximity of the top of the identification marker for that accessory module. There is no physical contact between the optical sensor subassembly 230 and the identification marker 282, when the optical sensor 236 moves into its proximal position with respect to that marker 282. Therefore, this is a touchless system, and no wear or soiling due to any type of mechanical contact should occur.

The optical sensor has a set of light emitting diodes (LEDs 231-234) which are used to illuminate the top of the identification marker 282. Only a single one of these LEDs needs to be illuminated at a time, and in general, the "leading LED" will be turned on for this step, which occurs at a step 324 on FIG. 13. In general, the identification sensor (the optical sensor 236) will be looking for a specific color, and more practically a relatively small range of those colors, such as a range of about 10% of the full scale RGB binary bit values, centered about a specific RGB value. (Of course, the optical sensor alternatively could be looking for a specific intensity threshold, or more practically a relatively small range of intensities, such as a band—centered about a specific intensity—of about 10% or perhaps less of the full scale of brightness as measured by the optical sensor 236.) The desired range, or threshold, of light intensity or of colors that will satisfy the identification routine used by the new design analytic autosampler can be adjusted as desired, as per the system designer's wishes for a specific purpose.

In addition, depending on how the movements of the transport motors are controlled, the typical maneuvering of the head unit 220 will allow for detection of an edge of the identification marker 282 to be detected, and at that detection point the transport motors will be turned off, meaning that the head module 220 has now successfully located the identification marker 282 for that particular accessory.

It will be understood that, since the identification sensor 236 is a color-detecting sensor, the optical sensor module 230 can be used to find all sorts of different colored identification markers, and these colors can be applied to a single edge of an otherwise all white color identification marker 282, or the entire marker could be a specific color. The various types of physical arrangements can be made into almost an unlimited number of combinations, when the color data is resolved for 16 bits (per red, green, and blue color plane), using an appropriate color sensor at 236. In addition, since there are four different LEDs, more than a single one can be turned on, if desired, or to achieve other effects (or merely create greater illumination), thus two or more of the four LEDs can be turned on simultaneously for illuminating the marker of an accessory module being sought. In general, only the leading LED will be turned on, but it depends on which direction the head module 220 is being moved at a particular time as to which one of those LEDs will actually be the "leading" LED. There are four LEDs, as seen in FIG. 12. The positioning of these LEDs 231-234 allows for any one of the four to be the leading LED, depending on whether or not the head module 220 is moving in the X-axis or the Y-axis, and in which direction of those two axes.

The identification markers of two different accessory modules can be of substantially the same color or brightness, if desired. If the modules are of the same type (e.g., if two modules both are 20 ml multi-sample trays), then perhaps the markers will by choice be of substantially the same color and brightness. Moreover, the identification markers of two different types of accessory modules can be selected by the system designer to intentionally be of substantially different colors and/or brightnesses. On the other hand, there is no rigorous requirement that the different types of accessory modules simply must exhibit different colored identification markers, so all such markers on all accessory modules could intentionally be of substantially the same appearance—they can all be bright white, for example.

The head module 220 is moved left or right until the identification optical sensor detects the edge, as indicated at a step 326 on FIG. 13. As noted above, that L/R direction is the X-axis, and in some situations it might be beneficial to be moving along the Y-axis for detecting an edge of the identification marker, for other purposes, or for other types of accessories.

Once the identification marker for the first accessory module has been found, a pop-up window will be generated on the user's monitor 126 with a message informing the user that a particular accessory has been detected at a particular location. It then offers the user to click "okay" to go to the next accessory location, or to select "cancel" to exit the automatic calibration mode. This function occurs at a step 328 on FIG. 13. A decision step 330 now determines whether the user selected okay or cancel, and if the user selected okay, a decision step 332 now determines the left/right position of the head module and determines if that was the end of travel for the physical rail. If not, then the logic flow is directed back to step 326 where the transport motor moves in the left/right direction (i.e., the X-axis) until the identification sensor detects the next edge for the next accessory module that is expected to be mounted to the rail.

If the user selected cancel at step 330, or if the end of the rail was found at step 332, then the logic flow is directed to a step 334 which exits the automatic calibration procedure. This step also homes all the axes and saves the calibration that was just determined The user could have selected a "manual" calibration mode at decision step 310. In that situation, a step 340 determines what the accessory module's identification number should be, with respect to the information that has been entered by the user into the main processor board 110. At a step 342, the transport motors are controlled, both the left/right and the forward/reverse (the X- and Y-axes), to the current motor stop position along the rail. This motor stop position is referred to by the designation "BL," on the flow chart of 300. A step 344 now moves the transport motors that control the up/down movements (i.e., for the Z-axis) to move the color optical sensor module 230 to the proper position that is proximal to the upper surface of the identification marker 282 for that type of accessory.

(It will be understood that the various types of accessories that can be mounted to the rail module 210 are generally of different physical sizes, and their identification markers can often be at different physical heights with respect to the bottom edge of the rail module. Therefore, it is typical that an up/down movement needs to occur to properly position the color positioning module 230 to its proper "measuring" distance above the expected (or predicted) elevation of the upper surface for the identification marker. In a preferred mode, that proximal measuring distance is about one-half inch of separation, although other proximal distances could of course be utilized if desired. In this description, the term "proximal measuring distance" means substantially the correct distance between the optical sensor and the identification marker, during which the "measuring step" is to occur, such that the autosampler system can now determine if a correct color range, or brightness range, has been found for making a determination that the substantially precise location has been discovered by the optical sensor for successfully calibrating the position of an accessory module.)

The identification (optical) sensor module 230 now illuminates at least one of the LEDs so that the edge detect sensor is also turned on, at a step 346. At a step 348, the head module 210 is moved along the left/right axis (i.e., X-axis) until the identification sensor 236 discovers the correct color values for the identification marker that is expected for this particular type of accessory module being sought. Once that has occurred, the transport motor will stop at its "BL" step position (for the stepper motor), and at a step 350, the BL calibration value will be updated for that particular accessory. That is the end of the manual calibration procedure.

Figure 14A:
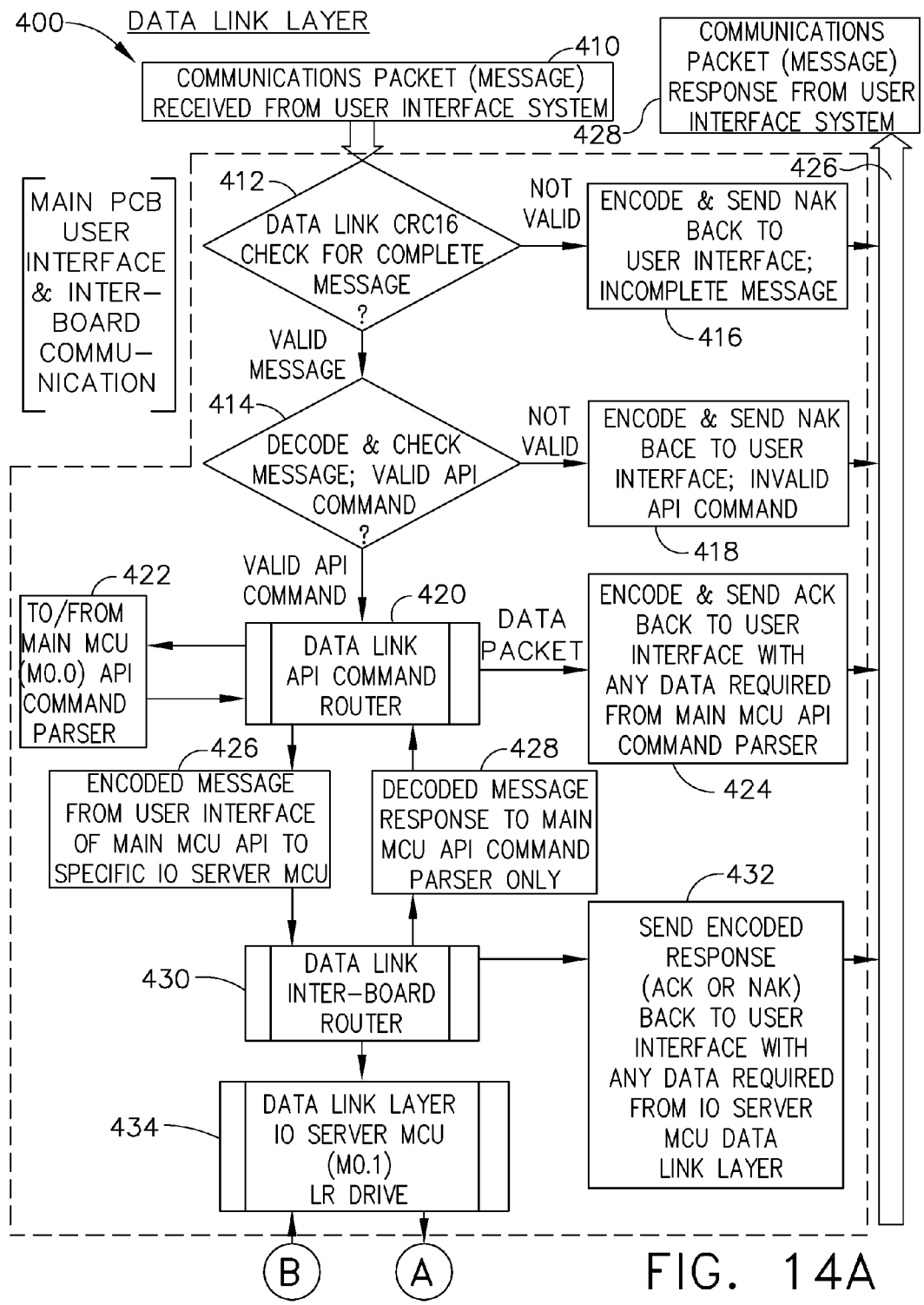
FIGS. 14A and 14B combined are a flow chart showing the steps performed by a "data link layer" routine that is used to communicate data packets to and from accessories, as used in the autosampler of FIG. 5.
Figure 14B:
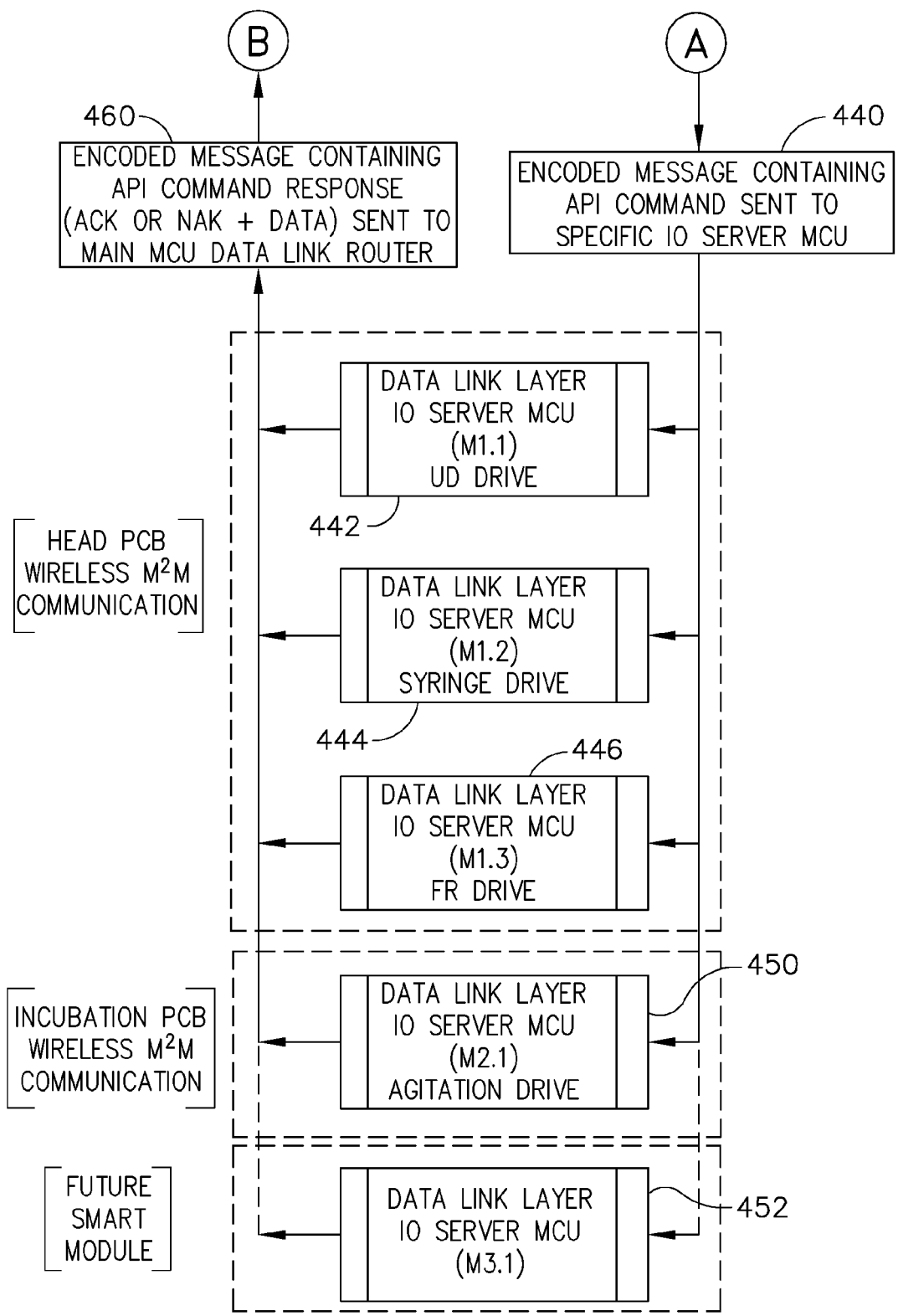

Another important routine used in the analytical autosampler 100 is referred to as a "data link layer" routine, and a flow chart of this routine is provided at FIG. 14, and is referred to in general by the reference numeral 400. FIG. 14 comprises two sheets, FIG. 14A and FIG. 14B. Flow chart 400 is mainly a software flow diagram, but it also groups the functional steps in a manner that makes sense from a hardware standpoint as well. For example, there are several microprocessors in one mode of the technology described herein.

A main processor board 110 essentially controls the entire unit, and that main processor board includes a main processor referred to as 112 on FIG. 4, and on the flow chart 400 is referred to as "M0.0." There is also a data link layer I/O server processor, and that device is referred to on flow chart 400 as "M0.1." That particular hardware device would diagrammatically be placed in the I/O interface 116 of the hardware block diagram of FIG. 4. However, if desired, it could be combined with the main processor M0.0, and all of the functions could be run by that one processor.

The head control module 130 on FIG. 4 also has a hardware printed circuit board, which is referred to as the "head PCB" (for printed circuit board) on the flow chart 400. This head board includes three different microprocessors in one mode of this technology, and those microprocessors are designated "M1.1", "M1.2", "M1.3". Each of those microprocessors controls one of the stepper motor drives on the head module 210, all under the control of the head control module 130. From a diagrammatic standpoint, all three of those microprocessors M1.1, M1.2, and M1.3 are part of the processing circuit 132 on FIG. 4.

Finally, each of the "smart" accessory modules will have some type of microprocessor or microcontroller circuit, and on the flow chart 400, the example illustrated is for an incubation accessory module, and it has a microcontroller or microprocessor unit referred to on FIG. 14 as "M2.1". This is for an agitation drive accessory. Future smart modules can be added to the system, as depicted on FIG. 14B. The next smart module added to the rail is referred to on the flow chart 400 as having a microprocessor designated as "M3.1". Additional smart modules can of course be added, and each one would have a different designation for its microprocessor or microcontroller device.

Referring now to top of FIG. 14A, it is assumed that the user's PC 124 is in communication with the main processor board 110 and the communications between the microprocessor circuit 112 and the user's PC 124 are transferred by data packets. When a communications packet is received from the user at a step 410, that message is transferred to a decision step 412, where an error message routine is performed. If the message is not deemed proper, the logic flow will be directed to a step 416 where a NAK (a "not-acknowledged") message is sent back to the user interface, and informing the user that an incomplete message had been received. That message is sent along a data flow arrow 426 to a step 428 that sends the communications packet response back to the user's PC 124, where it is displayed.

Assuming a valid message was received at step 412, a decision step 414 now decodes the message and checks to see if a valid "API command" has been received. In this flow chart 400, the designation "API" stands for "application program interface," and such commands are expected to be in a particular format and protocol. If a non-valid API command has been received, then a step 418 will encode a message back to the user and send a NAK, informing the user that an invalid API command had been received. That message is sent through the data flow 426 and through the communications packet block 428.

If a valid API command was received at 414, then a step 420 now executes a data link function which acts as a router for API commands. Most of the commands will be sent to the main microprocessor unit (the M0.0 unit) using an API command parser function at a step 422. This is a bi-directional communication, because in general once a command is received by the main processor board, the microprocessor 112 will be expected to respond with some type of message or function that will control a physical output. Part of the API command router routine 420 will be to send a data packet back to the user's PC. This occurs at a step 424 that encodes the message and sends an "ACK" (for acknowledge) back to the user interface, along with any data required from the main processing unit M0.0.

The main processor board can also send commands to the head module 210 and any of the accessory modules that are mounted to the autosampler 100. In that situation, a step 426 will encode messages from the user interface that will be processed and sent to a specific I/O server microprocessor unit. This occurs using a data link inter-board router function at a step 430. When such a command is received, an encoded response, either an ACK or a NAK, is sent back to the user interface with any data required, at a step 432.

If the user's command requires movements by any of the transport motors, then the command will be sent to the data link layer I/O server microprocessor M0.1, at a step 434. This particular microprocessor controls a stepper motor drive for the left/right drive (i.e., for the X-axis). In the illustrated example in the above figures, this microprocessor M0.1 is part of the main processor board 110.

Other commands that are to be acted on by other transport motors will be sent by an encoded message to one of the accessory modules or to the head module, using a radio signal generated by the M2M chip set for sending wireless signals, under control of a step 440. The flow chart has now entered FIG. 14B. If the command is to be acted upon by the head control module 130, then it is sent to one of the three drive motors, and acted on by one of the three microprocessors M1.1, M1.2, or M1.3. These are controlled by functions 442, 444, or 446 respectively on the flow chart 400. The processing circuit controlled by the step 442 is for the up/down drive stepper motor, the processing circuit controlled by the step 444 is for the syringe drive stepper motor, and the processing circuit controlled by the step 446 is for the forward/reverse stepper motor. Once those functions have been received and executed, an encoded message sending an API command response is sent back to the main controller 110, via a function step 460.

If the original API command is to be sent to the agitation drive, which is controlled by the microprocessor M2.1, then that message will be received by a data link layer I/O server function at a step 450. Once that has occurred, an encoded message containing the API command response will be sent back to the main processor by the functional step 460.

As noted above, there can be a future smart module that is designated having a microprocessor M3.1. That will be controlled by functions at a step 452 on FIG. 14B. This acts just like the other data link layer stepper motor controllers and functions, with regard to the data packet messages it receives and sends, using a wireless transmitter/receiver circuit.

As noted above, future smart modules can be added as accessories to the main rail without requiring any additional data cables to be installed, because of the wireless control signals being sent between the master wireless transmitter/receiver 128 and all of the client wireless transmitter/receivers. This is a huge advantage to quick and easy expansion of the capabilities of a particular analytic autosampler of the new design.

It will be understood that the head module 220 does not always contain a syringe, although the illustrated embodiment of FIG. 5 includes a fitting at 222 for holding a sample-extracting syringe. This is only an example of the capabilities of the overall system design. Instead of holding a sample syringe, the head module, for example, could be a SPME (Solid Phase Micro Extraction) Fiber, a gripper assembly, or a coupling device for a tool changer. Certainly other types of devices could be mounted to, or included in, the head module without departing from the inventive principles disclosed herein.

Additional details about chemical analytical instruments are provided in other patent documents filed by EST Analytical, Inc. For example, U.S. Pat. No. 7,803,635 is titled, "Purge and trap concentrator with sparge vessel," and is assigned to EST Analytical, Inc.; U.S. Pat. No. 7,951,609 is titled, "Purge and trap concentrator with sparge vessel," and is assigned to EST Analytical, Inc.; U.S. Pat. No. 8,062,905 is titled, "Purge and trap concentrator with sparge vessel," and is assigned to EST Analytical, Inc.; U.S. Pat. No. 8,075,842 is titled, "Analytical chemical sampling system with sparge vessel," and is assigned to EST Analytical, Inc.; and U.S. Pat. No. 8,092,744 is titled, "Analytical chemical sampling system with bypass mode," and is assigned to EST Analytical, Inc. These patent documents are incorporated herein by reference in their entirety.

It will be understood that the logical operations described in relation to the flow charts of FIGS. 13 and 14 can be implemented using sequential logic (such as by using microprocessor technology), or using a logic state machine, or perhaps by discrete logic; it even could be implemented using parallel processors. One preferred embodiment may use a microprocessor or microcontroller (e.g., microprocessor 22) to execute software instructions that are stored in memory cells within an ASIC. In fact, the entire microprocessor (or microcontroller), along with RAM and executable ROM, may be contained within a single ASIC, in one mode of the technology disclosed herein. Of course, other types of circuitry could be used to implement these logical operations depicted in the drawings without departing from the principles of the technology disclosed herein. In any event, some type of processing circuit will be provided, whether it is based on a microprocessor, a logic state machine, by using discrete logic elements to accomplish these tasks, or perhaps by a type of computation device not yet invented; moreover, some type of memory circuit will be provided, whether it is based on typical RAM chips, EEROM chips (including Flash memory), by using discrete logic elements to store data and other operating information (such as the control data stored, for example, in memory circuit 24), or perhaps by a type of memory device not yet invented.

It will also be understood that the precise logical operations depicted in the flow charts of FIGS. 13 and 14 and discussed above, could be somewhat modified to perform similar, although not exact, functions without departing from the principles of the technology disclosed herein. The exact nature of some of the decision steps and other commands in these flow charts are directed toward specific future models of autosampler systems (those involving EST brand chemical autosamplers, for example) and certainly similar, but somewhat different, steps would be taken for use with other models or brands of chemical autosampler systems in many instances, with the overall inventive results being the same.

As used herein, the term "proximal" can have a meaning of closely positioning one physical object with a second physical object, such that the two objects are perhaps adjacent to one another, although it is not necessarily required that there be no third object positioned therebetween. In the technology disclosed herein, there may be instances in which a "male locating structure" is to be positioned "proximal" to a "female locating structure." In general, this could mean that the two male and female structures are to be physically abutting one another, or this could mean that they are "mated" to one another by way of a particular size and shape that essentially keeps one structure oriented in a predetermined direction and at an X-Y (e.g., horizontal and vertical) position with respect to one another, regardless as to whether the two male and female structures actually touch one another along a continuous surface. Or, two structures of any size and shape (whether male, female, or otherwise in shape) may be located somewhat near one another, regardless if they physically abut one another or not; such a relationship could still be termed "proximal." Or, two or more possible locations for a particular point can be specified in relation to a precise attribute of a physical object, such as being "near" or "at" the end of a stick; all of those possible near/at locations could be deemed "proximal" to the end of that stick. Moreover, the term "proximal" can also have a meaning that relates strictly to a single object, in which the single object may have two ends, and the "distal end" is the end that is positioned somewhat farther away from a subject point (or area) of reference, and the "proximal end" is the other end, which would be positioned somewhat closer to that same subject point (or area) of reference.

It will be understood that the various components that are described and/or illustrated herein can be fabricated in various ways, including in multiple parts or as a unitary part for each of these components, without departing from the principles of the technology disclosed herein. For example, a component that is included as a recited element of a claim hereinbelow may be fabricated as a unitary part; or that component may be fabricated as a combined structure of several individual parts that are assembled together. But that "multi-part component" will still fall within the scope of the claimed, recited element for infringement purposes of claim interpretation, even if it appears that the claimed, recited element is described and illustrated herein only as a unitary structure.

All documents cited in the Background and in the Detailed Description are, in relevant part, incorporated herein by reference; the citation of any document is not to be construed as an admission that it is prior art with respect to the technology disclosed herein.

The foregoing description of a preferred embodiment has been presented for purposes of illustration and description. It is not intended to be exhaustive or to limit the technology disclosed herein to the precise form disclosed, and the technology disclosed herein may be further modified within the spirit and scope of this disclosure. Any examples described or illustrated herein are intended as non-limiting examples, and many modifications or variations of the examples, or of the preferred embodiment(s), are possible in light of the above teachings, without departing from the spirit and scope of the technology disclosed herein. The embodiment(s) was chosen and described in order to illustrate the principles of the technology disclosed herein and its practical application to thereby enable one of ordinary skill in the art to utilize the technology disclosed herein in various embodiments and with various modifications as are suited to particular uses contemplated. This application is therefore intended to cover any variations, uses, or adaptations of the technology disclosed herein using its general principles. Further, this application is intended to cover such departures from the present disclosure as come within known or customary practice in the art to which this technology disclosed herein pertains and which fall within the limits of the appended claims.

What is claimed is:

1. A chemical sampling apparatus, comprising:
   (a) a main computer station, having a first processing circuit, a first memory circuit, and a first wireless communications circuit;
   (b) a head module that includes a chemical sampling device, said head module having a second processing circuit, a second memory circuit, and a second wireless communications circuit;
   (c) a first accessory module having a third processing circuit, a third memory circuit, and a third wireless communications circuit;
   (d) a power source that provides electrical energy to said main computer station, said head module, and said first accessory module;
   wherein:
   (e) said first processing circuit communicates first data signals with said second processing circuit using said first and second wireless communications circuits, and without the use of data cables between said main computer station and said head module; and
   (f) said first processing circuit communicates second data signals with said third processing circuit using said first and third wireless communications circuits, without the use of any data cable between said main computer station and said first accessory module.

2. The apparatus of claim 1, wherein said head module includes:
   a first motorized transport device that physically moves said head module along a direction that is parallel to a longitudinal axis of a longitudinal member, in which said first accessory module is installed on said longitudinal member.

3. The apparatus of claim 2, further comprising:
   (a) a sensor that is in communication with said second processing circuit, said sensor being mounted on said head module; and
   (b) a first identification area at a predetermined location on said first accessory module that can be detected by said sensor when said head module is moved, using said first motorized transport device, to a suitable first physical position with respect to a second physical position of said first accessory module.

4. The apparatus of claim 3, wherein:
   (a) said first identification area exhibits at least one of (i) a first predetermined color and (ii) a first predetermined brightness; and
   (b) said sensor comprises an optical sensor that discerns said at least one of (i) a first predetermined color and (ii) a first predetermined brightness.

5. The apparatus of claim 3, wherein:
   (a) said first accessory module is initially attached at an unknown position on said longitudinal member;
   (b) said first identification area comprises a first identifier marking on said first accessory module; and
   (c) said first and second processing circuits are programmed with computer code to perform functions of executing a position calibration routine that controls movements of said head module, in which:
      (i) said head module is moved to predicted locations along said longitudinal rail while searching for said identifier marking on said first accessory module;
      (ii) after finding said first identifier marking, then verifying a physical position of said first accessory module with respect to said longitudinal rail; and
      (iii) thereby calibrating the physical position of said first accessory module.

6. The apparatus of claim 2, further comprising:
   a second motorized transport device that physically moves said head module along a second axis that is perpendicular to said longitudinal axis of said longitudinal member; and
   a third motorized transport device that physically moves said head module along a third axis that is perpendicular both to said longitudinal axis of said longitudinal member and to said second axis;
   wherein said head module movements are in three linear axes, using said first, second, and third motorized transport devices, for moving said head module into at least one position for physically interacting with said first accessory module.

7. The apparatus of claim 2, further comprising:
(a) a second accessory module having a fourth processing circuit, a fourth memory circuit, and a fourth wireless communications circuit;
wherein:
(b) said first accessory module is installed on said longitudinal member;
(c) said second accessory module is installed on said longitudinal member;
(d) said first processing circuit communicates third data signals with said fourth processing circuit using said first and fourth wireless communications circuits, without the use of any data cable between said main computer station and said second accessory module.

8. The apparatus of claim 7, further comprising:
(a) a third accessory module having a fifth processing circuit, a fifth memory circuit, and a fifth wireless communications circuit;
wherein:
(b) said third accessory module is installed on said longitudinal member; and
(c) said first processing circuit communicates fourth data signals with said fifth processing circuit using said first and fifth wireless communications circuits, without the use of any data cable between said main computer station and said third accessory module.

9. The apparatus of claim 7, further comprising:
(a) a sensor that is in communication with said second processing circuit, said sensor being mounted on said head module;
(b) a first identification area at a predetermined location on said first accessory module that can be detected by said sensor when said head module is moved, using said first motorized transport device, to a suitable first physical position with respect to a second physical position of said first accessory module; and
(c) a second identification area at a predetermined location on said second accessory module that can be detected by said sensor when said head module is moved, using said first motorized transport device, to a suitable third physical position with respect to a fourth physical position of said second accessory module.

10. The apparatus of claim 9, wherein:
(a) said first and second accessory modules are initially attached at unknown positions on said longitudinal member;
(b) said first identification area comprises a first identifier marking on said first accessory module;
(c) said second identification area comprises a second identifier marking on said second accessory module; and
(d) said first and second processing circuits are programmed with computer code to perform functions of executing a position calibration routine that controls movements of said head module, in which:
  (i) said head module is moved to predicted locations along said longitudinal rail while searching for said first and second identifier markings on each of said first and second accessory modules;
  (ii) after finding said first identifier marking, then verifying a physical position of said first accessory module with respect to said longitudinal rail;
  (iii) after finding said second identifier marking, then verifying a physical position of said second accessory module with respect to said longitudinal rail; and
  (iv) thereby calibrating the physical positions of both said first and second accessory modules.

11. The apparatus of claim 1, wherein there are N accessory modules including the first and at least one Nth accessory module, wherein N is a positive integer greater than 1 and includes all integers from 2 through a maximum value Nmax, inclusive, said at least one Nth accessory module having an Xth processing circuit, an Xth memory circuit, and an Xth wireless communications circuit, in which X is a positive integer equal to N+2;
wherein:
(a) said first accessory module is installed on said longitudinal member;
(b) said at least one Nth accessory module is installed on said longitudinal member;
(c) said first processing circuit communicates Yth data signals with said Xth processing circuit using said first and Xth wireless communications circuits, without the use of any data cable between said main computer station and said at least one Nth accessory module, in which Y is a positive integer equal to N+1.

12. The apparatus of claim 1, further comprising:
(a) a sensor that is in communication with said second processing circuit, said sensor being mounted on said head module; and
(b) a first identification area at a predetermined location on said first accessory module that can be detected by said sensor when said head module is moved to a suitable first physical position with respect to a second physical position of said first accessory module.

13. The apparatus of claim 12, wherein:
(a) said first identification area exhibits at least one of (i) a first predetermined color and (ii) a first predetermined brightness; and
(b) said sensor comprises an optical sensor that discerns said at least one of (i) a first predetermined color and (ii) a first predetermined brightness.

14. A chemical sampling apparatus, comprising:
(a) a main computer station, having a first processing circuit, a first memory circuit, and a first wireless communications circuit;
(b) a head module that includes a chemical sampling device, said head module having a second processing circuit, a second memory circuit, and a second wireless communications circuit;
(c) at least two accessory modules, each having an accessory module processing circuit, an accessory module memory circuit, and an accessory module wireless communications circuit;
(d) at least one power source that provides electrical energy to said main computer station, said head module, and said at least two accessory modules;
wherein:
(e) said first processing circuit communicates first data signals with said second processing circuit using said first and second wireless communications circuits, and without the use of data cables between said main computer station and said head module; and
(f) said first processing circuit communicates accessory module data signals with a respective one of each of said accessory module processing circuits using at least one of said first and second wireless communications circuits, and using a respective one of said accessory module wireless communications circuits, without the use of any data cable between said main computer station, said head module, and said at least two accessory modules.

15. The apparatus of claim 14, wherein: said at least two accessory modules are positioned at virtually any physical location in said chemical sampling apparatus, as per the user's desire.

16. The apparatus of claim 14, further comprising a mounting member to which said head module is movably attached.

17. The apparatus of claim 16, wherein said head module includes a first motorized transport device that physically moves said head module along a direction that is parallel to a longitudinal axis of said mounting member.

18. The apparatus of claim 16, wherein at least one of said at least two accessory modules are attached to said mounting member.

\* \* \* \* \*